(12) United States Patent
Lin et al.

(10) Patent No.: US 9,200,306 B2
(45) Date of Patent: Dec. 1, 2015

(54) METHODS FOR PRODUCTION AND PURIFICATION OF POLYPEPTIDES

(71) Applicant: TSINGHUA UNIVERSITY, Beijing (CN)

(72) Inventors: Zhanglin Lin, Beijing (CN); Wanghui Xu, Beijing (CN); Lei Xing, Beijing (CN); Lingli Zeng, Beijing (CN); Bihong Zhou, Beijing (CN); Qing Zhao, Beijing (CN); Wei Wu, Tianjin (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 13/836,817

(22) Filed: Mar. 15, 2013

(65) Prior Publication Data

US 2014/0106399 A1 Apr. 17, 2014

(30) Foreign Application Priority Data

Oct. 12, 2012 (CN) .................. PCT/CN2012/082879

(51) Int. Cl.
*C12P 21/06* (2006.01)
*C12N 1/00* (2006.01)
*C07K 14/00* (2006.01)
*C07K 14/575* (2006.01)
*C07K 14/605* (2006.01)

(52) U.S. Cl.
CPC ............... *C12P 21/06* (2013.01); *C07K 14/00* (2013.01); *C07K 14/57581* (2013.01); *C07K 14/605* (2013.01); *C12N 1/00* (2013.01); *C07K 2319/01* (2013.01); *C07K 2319/50* (2013.01); *C07K 2319/70* (2013.01)

(58) Field of Classification Search
None
See application file for complete search history.

(56) References Cited

U.S. PATENT DOCUMENTS

| | | | | |
|---|---|---|---|---|
| 5,821,088 | A * | 10/1998 | Darzins et al. ............... | 435/69.7 |
| 6,818,611 | B1 * | 11/2004 | Altman ........................ | 514/2.4 |
| 6,861,403 | B2 * | 3/2005 | Sanders ...................... | 435/69.1 |
| 8,022,178 | B2 * | 9/2011 | Horii et al. .................. | 530/324 |
| 8,124,588 | B2 * | 2/2012 | Seeger et al. ................ | 514/14.6 |
| 2003/0162259 | A1 * | 8/2003 | Sheppard et al. ............ | 435/69.7 |
| 2004/0142429 | A1 * | 7/2004 | Grant et al. .................. | 435/69.7 |
| 2006/0263855 | A1 * | 11/2006 | Wood et al. .................. | 435/69.7 |
| 2009/0029412 | A1 * | 1/2009 | Cheng et al. ................. | 435/68.1 |
| 2012/0009624 | A1 * | 1/2012 | Sommer-Knudsen et al. ............................ | 435/69.7 |
| 2012/0088268 | A1 * | 4/2012 | Hummerich et al. ........ | 435/68.1 |
| 2012/0184714 | A1 * | 7/2012 | Sun et al. ..................... | 530/353 |
| 2012/0277410 | A1 * | 11/2012 | Dunker et al. ............... | 530/370 |
| 2013/0065278 | A1 * | 3/2013 | Johansson et al. .......... | 435/69.7 |

OTHER PUBLICATIONS

Y. Li, "Recombinant production of antimicrobial peptides in *Escherichia coli*: A review", Protein Expression and Purification, vol. 80, pp. 260-267, 2011.*

Park et al., "Enhanced stability of heterologous proteins by supramolecular self-assembly", Applied Microbiology and Biotechnology, vol. 75, pp. 347-355, 2007.*

* cited by examiner

*Primary Examiner* — Robert Mondesi
*Assistant Examiner* — Richard Ekstrom
(74) *Attorney, Agent, or Firm* — Rothwell, Figg, Ernst & Manbeck P.C.

(57) ABSTRACT

The present invention relates to a method for production and purification of polypeptides. In particular, the present invention relates to a fusion protein comprising a solubility-enhancing peptide tag moiety, a self-aggregating peptide moiety and a moiety of target peptide and to a method for production and purification of target peptides through expressing said fusion protein.

34 Claims, 10 Drawing Sheets

SEQUENCE LISTING

<160> NUMBER OF SEQ ID NOS: 47

<210> SEQ ID NO 1
<211> LENGTH: 16
<212> TYPE: PRT
<213> ORGANISM: Artificial
<220> FEATURE:
<223> OTHER INFORMATION: ELK16

<400> SEQUENCE: 1

Leu Glu Leu Glu Leu Lys Leu Lys Leu Glu Leu Glu Leu Lys Leu Lys
1               5                   10                  15

<210> SEQ ID NO 2
<211> LENGTH: 18
<212> TYPE: PRT
<213> ORGANISM: Artificial
<220> FEATURE:
<223> OTHER INFORMATION: 18A

<400> SEQUENCE: 2

Glu Trp Leu Lys Ala Phe Tyr Glu Lys Val Leu Glu Lys Leu Lys Glu
1               5                   10                  15

Leu Phe

<210> SEQ ID NO 3
<211> LENGTH: 8
<212> TYPE: PRT
<213> ORGANISM: Artificial
<220> FEATURE:
<223> OTHER INFORMATION: L6KD

<400> SEQUENCE: 3

Leu Leu Leu Leu Leu Leu Lys Asp
1               5

<210> SEQ ID NO 4
<211> LENGTH: 8
<212> TYPE: PRT
<213> ORGANISM: Artificial
<220> FEATURE:
<223> OTHER INFORMATION: L6KK

<400> SEQUENCE: 4

Leu Leu Leu Leu Leu Leu Lys Lys
1               5

<210> SEQ ID NO 5
<211> LENGTH: 8
<212> TYPE: PRT
<213> ORGANISM: Artificial
<220> FEATURE:
<223> OTHER INFORMATION: DKL6

<400> SEQUENCE: 5

Asp Lys Leu Leu Leu Leu Leu Leu
1               5

<210> SEQ ID NO 6
<211> LENGTH: 198
<212> TYPE: PRT
<213> ORGANISM: Artificial
<220> FEATURE:
<223> OTHER INFORMATION: intein

<400> SEQUENCE: 6

```
Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
                35                  40                  45

Arg Leu Phe His Ser Gly Glu His Pro Val Tyr Thr Val Arg Thr Val
        50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
                100                 105                 110

Asp Cys Ala Gly Phe Ala Arg Gly Lys Pro Glu Phe Ala Pro Thr Thr
            115                 120                 125

Tyr Thr Val Gly Val Pro Gly Leu Val Arg Phe Leu Glu Ala His His
        130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Ala
        195

<210> SEQ ID NO 7
<211> LENGTH: 5
<212> TYPE: PRT
<213> ORGANISM: Artificial
<220> FEATURE:
<223> OTHER INFORMATION: EK recognization site

<400> SEQUENCE: 7

Asp Asp Asp Asp Lys
1               5

<210> SEQ ID NO 8
<211> LENGTH: 16
<212> TYPE: PRT
<213> ORGANISM: Artificial
<220> FEATURE:
<223> OTHER INFORMATION: PT peptide

<400> SEQUENCE: 8

Pro Thr Pro Pro Thr Thr Pro Thr Pro Pro Thr Pro Thr Pro Pro Thr
1               5                   10                  15

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
gcgatacata tgcaccatca ccatca                                              26

<210> SEQ ID NO 10
```

```
<211> LENGTH: 43
<212> TYPE: DNA
<213> ORGANISM: Artificial
<220> FEATURE:
<223> OTHER INFORMATION: primer

<400> SEQUENCE: 10
gcatctcccg tgatgcacat tcgcatattc gtattctggc ccc                    43

<210> SEQ ID NO 11
<211> LENGTH: 41
<212> TYPE: DNA
<213> ORGANISM: Artificial
<220> FEATURE:
<223> OTHER INFORMATION: primer

<400> SEQUENCE: 11
ggggccagaa tacgaatatg cgaatgtgca tcacgggaga t                      41

<210> SEQ ID NO 12
<211> LENGTH: 34
<212> TYPE: DNA
<213> ORGANISM: Artificial
<220> FEATURE:
<223> OTHER INFORMATION: primer

<400> SEQUENCE: 12
attttaaagc ttagcgtggc tgacgaaccc gttc                              34

<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13
gcgatacata tgcaccatca ccatca                                       26

<210> SEQ ID NO 14
<211> LENGTH: 34
<212> TYPE: DNA
<213> ORGANISM: Artificial
<220> FEATURE:
<223> OTHER INFORMATION: primer

<400> SEQUENCE: 14
attttaaagc ttagcgtggc tgacgaaccc gttc                              34

<210> SEQ ID NO 15
<211> LENGTH: 27
<212> TYPE: DNA
<213> ORGANISM: Artificial
<220> FEATURE:
<223> OTHER INFORMATION: primer

<400> SEQUENCE: 15
agttacatat gagcgataaa attattc                                      27

<210> SEQ ID NO 16
<211> LENGTH: 89
<212> TYPE: DNA
<213> ORGANISM: Artificial
<220> FEATURE:
<223> OTHER INFORMATION: primer

<400> SEQUENCE: 16
```

```
tcacgactag tgcatctccc gtgatgcaca ttcgcatgat atcagaacct gaacctgaac    60
cagatctcgc caggttagcg tcgaggaac                                      89
```

<210> SEQ ID NO 17
<211> LENGTH: 65
<212> TYPE: DNA
<213> ORGANISM: Artificial
<220> FEATURE:
<223> OTHER INFORMATION: primer

<400> SEQUENCE: 17

```
agtcaagatc tgggtaccga cgacgacgac aaggatatca tgcgaatgtg catcacggga    60
gatgc                                                                65
```

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18

```
gtcggaagct tagcgtggct gacgaacccg ttc                                  33
```

<210> SEQ ID NO 19
<211> LENGTH: 31
<212> TYPE: PRT
<213> ORGANISM: Homo sapiens

<400> SEQUENCE: 19

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 20
<211> LENGTH: 93
<212> TYPE: DNA
<213> ORGANISM: Artificial
<220> FEATURE:
<223> OTHER INFORMATION: GLP-1 polynucleotide

<400> SEQUENCE: 20

```
catgcagaag gcacctttac cagcgatgtt agcagctatc tggaaggtca ggcagcaaaa    60
gaatttattg catggctggt taaaggtcgt ggt                                  93
```

<210> SEQ ID NO 21
<211> LENGTH: 32
<212> TYPE: PRT
<213> ORGANISM: Homo sapiens

<400> SEQUENCE: 21

```
Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

<210> SEQ ID NO 22
<211> LENGTH: 96
<212> TYPE: DNA
<213> ORGANISM: Artificial
<220> FEATURE:

<223> OTHER INFORMATION: BNP polynucleotide

<400> SEQUENCE: 22

```
tctccgaaaa tggttcaggg ttctggttgc ttcggtcgta aaatggaccg tatctcttct    60
tcttctggtc tgggttgcaa agttctgcgt cgtcac                              96
```

<210> SEQ ID NO 23
<211> LENGTH: 39
<212> TYPE: PRT
<213> ORGANISM: Homo sapiens

<400> SEQUENCE: 23

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```

<210> SEQ ID NO 24
<211> LENGTH: 117
<212> TYPE: DNA
<213> ORGANISM: Artificial
<220> FEATURE:
<223> OTHER INFORMATION: Ex-4 polynucleotide

<400> SEQUENCE: 24

```
catggtgaag gtacctttac cagcgatctg agcaaacaga tggaagaaga agcagttcgt    60
ctgtttattg aatggctgaa aaatggtggt ccgagcagcg gtgcaccgcc gccgagc      117
```

<210> SEQ ID NO 25
<211> LENGTH: 66
<212> TYPE: PRT
<213> ORGANISM: Homo sapiens

<400> SEQUENCE: 25

```
Tyr Ser Ser Asp Thr Thr Pro Cys Cys Phe Ala Tyr Ile Ala Arg Pro
1               5                   10                  15

Leu Pro Arg Ala His Ile Lys Glu Tyr Phe Tyr Thr Ser Gly Lys Cys
            20                  25                  30

Ser Asn Pro Ala Val Val Phe Val Thr Arg Lys Asn Arg Gln Val Cys
        35                  40                  45

Ala Asn Pro Glu Lys Lys Trp Val Arg Glu Tyr Ile Asn Ser Leu Glu
    50                  55                  60

Met Ser
65
```

<210> SEQ ID NO 26
<211> LENGTH: 198
<212> TYPE: DNA
<213> ORGANISM: Artificial
<220> FEATURE:
<223> OTHER INFORMATION: CCL-5 polynucleotide

<400> SEQUENCE: 26

```
tactcttctg acaccacccc gtgctgcttc gcttacatcg ctcgtccgct gccgcgtgct    60
cacatcaaag aatacttcta cacctctggt aaatgctcta accggctgt tgttttcgtt   120 acccgtaaaa accgtcaggt ttgcgctaac ccggaaaaaa atgggttcg tgaatacatc   180 aactctctgg aaatgtct                                                 198
```

<210> SEQ ID NO 27
<211> LENGTH: 67
<212> TYPE: PRT
<213> ORGANISM: Homo sapiens

<400> SEQUENCE: 27

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn
65

<210> SEQ ID NO 28
<211> LENGTH: 201
<212> TYPE: DNA
<213> ORGANISM: Artificial
<220> FEATURE:
<223> OTHER INFORMATION: SDF-1a polynucleotide

<400> SEQUENCE: 28
aaaccggttt ctctgtctta ccgttgcccg tgccgtttct tcgaatctca cgttgctcgt      60
gctaacgtta aacacctgaa aatcctgaac accccgaact gcgctctgca aatcgttgct    120
cgtctgaaaa acaacaaccg tcaggtttgc atcgacccga aactgaaatg gatccaggaa    180
tacctggaaa aagctctgaa c                                              201

<210> SEQ ID NO 29
<211> LENGTH: 70
<212> TYPE: PRT
<213> ORGANISM: Homo sapiens

<400> SEQUENCE: 29

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 30
<211> LENGTH: 210
<212> TYPE: DNA
<213> ORGANISM: Artificial
<220> FEATURE:
<223> OTHER INFORMATION: IGF-1a polynucleotide

<400> SEQUENCE: 30
ggtccggaaa ccctgtgcgg tgctgaactg gttgacgctc tgcagttcgt ttgcggtgac      60
cgtggtttct acttcaacaa accgaccggt tacggttctt cttctcgtcg tgctccgcag    120

```
accggtatcg ttgacgaatg ctgcttccgt tcttgcgacc tgcgtcgtct ggaaatgtac      180
tgcgctccgc tgaaaccggc taaatctgct                                       210
```

<210> SEQ ID NO 31
<211> LENGTH: 146
<212> TYPE: PRT
<213> ORGANISM: Homo sapiens

<400> SEQUENCE: 31

```
Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

<210> SEQ ID NO 32
<211> LENGTH: 438
<212> TYPE: DNA
<213> ORGANISM: Artificial
<220> FEATURE:
<223> OTHER INFORMATION: Lep polynucleotide

<400> SEQUENCE: 32

```
gttccgatcc agaaagttca ggacgacacc aaaaccctga tcaaaaccat cgttacccgt      60
atcaacgaca tctctcacac ccagtctgtt tcttctaaac agaaagttac cggtctggac     120
ttcatcccgg gtctgcaccc gatcctgacc ctgtctaaaa tggaccagac tctcgctgtc     180
taccagcaaa tcctgacctc tatgccgtct cgtaacgtta tccagatcag taacgacctg     240
gaaaacctgc gtgacctgct gcacgttctg gctttctcta atcttgcca cctgccgtgg      300 gcttctggtc tggaaaccct ggactctctg ggtggtgttc tggaagcttc tggttactct     360
accgaagttg ttgctctgtc tcgtctgcag ggttctctgc aggacatgct gtggcagctg     420
gacctgtctc cgggttgc                                                   438
```

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33

```
agcatcatat gcatgcagaa ggcacctttt                                      29
```

<210> SEQ ID NO 34
<211> LENGTH: 51
<212> TYPE: DNA
<213> ORGANISM: Artificial
<220> FEATURE:
<223> OTHER INFORMATION: primer

<400> SEQUENCE: 34
agtcaagatc tgggtaccga cgacgacgac aagcatgcag aaggcacctt t    51

<210> SEQ ID NO 35
<211> LENGTH: 52
<212> TYPE: DNA
<213> ORGANISM: Artificial
<220> FEATURE:
<223> OTHER INFORMATION: primer

<400> SEQUENCE: 35
agcatactag tgcatctccc gtgatgcaga tatcaccacg acctttaacc ag    52

<210> SEQ ID NO 36
<211> LENGTH: 108
<212> TYPE: PRT
<213> ORGANISM: Artificial
<220> FEATURE:
<223> OTHER INFORMATION: Trx

<400> SEQUENCE: 36

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala
            100                 105

<210> SEQ ID NO 37
<211> LENGTH: 324
<212> TYPE: DNA
<213> ORGANISM: Artificial
<220> FEATURE:
<223> OTHER INFORMATION: Trx polynucleotide

<400> SEQUENCE: 37
agcgataaaa ttattcacct gactgacgac agttttgaca cggatgtact caaagcggac    60
ggggcgatcc tcgtcgattt ctgggcagag tggtgcggtc cgtgcaaaat gatcgccccg   120
attctggatg aaatcgctga cgaatatcag ggcaaactga ccgttgcaaa actgaacatc   180
gatcaaaacc ctggcactgc gccgaaatat ggcatccgtg gtatcccgac tctgctgctg   240
ttcaaaaacg gtgaagtggc ggcaaccaaa gtgggtgcac tgtctaaagg tcagttgaaa   300
gagttcctcg acgctaacct ggcg                                          324

<210> SEQ ID NO 38
<211> LENGTH: 219
<212> TYPE: PRT
<213> ORGANISM: Artificial
<220> FEATURE:
<223> OTHER INFORMATION: GST

<400> SEQUENCE: 38

Ser Pro Ile Leu Gly Tyr Trp Lys Ile Lys Gly Leu Val Gln Pro Thr
1               5                   10                  15
Arg Leu Leu Leu Glu Tyr Leu Glu Glu Lys Tyr Glu Glu His Leu Tyr
            20                  25                  30
Glu Arg Asp Glu Gly Asp Lys Trp Arg Asn Lys Lys Phe Glu Leu Gly
        35                  40                  45
Leu Glu Phe Pro Asn Leu Pro Tyr Tyr Ile Asp Gly Asp Val Lys Leu
    50                  55                  60
Thr Gln Ser Met Ala Ile Ile Arg Tyr Ile Ala Asp Lys His Asn Met
65                  70                  75                  80
Leu Gly Gly Cys Pro Lys Glu Arg Ala Glu Ile Ser Met Leu Glu Gly
                85                  90                  95
Ala Val Leu Asp Ile Arg Tyr Gly Val Ser Arg Ile Ala Tyr Ser Lys
            100                 105                 110
Asp Phe Glu Thr Leu Lys Val Asp Phe Leu Ser Lys Leu Pro Glu Met
        115                 120                 125
Leu Lys Met Phe Glu Asp Arg Leu Cys His Lys Thr Tyr Leu Asn Gly
    130                 135                 140
Asp His Val Thr His Pro Asp Phe Met Leu Tyr Asp Ala Leu Asp Val
145                 150                 155                 160
Val Leu Tyr Met Asp Pro Met Cys Leu Asp Ala Phe Pro Lys Leu Val
                165                 170                 175
Cys Phe Lys Lys Arg Ile Glu Ala Ile Pro Gln Ile Asp Lys Tyr Leu
            180                 185                 190
Lys Ser Ser Lys Tyr Ile Ala Trp Pro Leu Gln Gly Trp Gln Ala Thr
        195                 200                 205
Phe Gly Gly Gly Asp His Pro Pro Lys Ser Asp
    210                 215

<210> SEQ ID NO 39
<211> LENGTH: 657
<212> TYPE: DNA
<213> ORGANISM: Artificial
<220> FEATURE:
<223> OTHER INFORMATION: GST polynucleotide

<400> SEQUENCE: 39
tcccctatac taggttattg gaaaattaag ggccttgtgc aacccactcg acttcttttg     60
gaatatcttg aagaaaaata tgaagagcat ttgtatgagc gcgatgaagg tgataaatgg    120
cgaaacaaaa agtttgaatt gggtttggag tttcccaatc ttccttatta tattgatggt    180
gatgttaaat taacacagtc tatggccatc atacgttata gctgacaa gcacaacatg    240
ttgggtggtt gtccaaaaga gcgtgcagag atttcaatgc ttgaaggagc ggttttggat    300
attagatacg gtgtttcgag aattgcatat agtaaagact tgaaactct caaagttgat    360
tttcttagca agctacctga atgctgaaaa atgttcgaag atcgtttatg tcataaaaca    420
tatttaaatg gtgatcatgt aacccatcct gacttcatgt tgtatgacgc tcttgatgtt    480
gttttataca tggacccaat gtgcctggat gcgttcccaa aattagtttg ttttaaaaaa    540

```
cgtattgaag ctatcccaca aattgataag tacttgaaat ccagcaagta tatagcatgg    600
cctttgcagg gctggcaagc cacgtttggt ggtggcgacc atcctccaaa atcggat       657
```

<210> SEQ ID NO 40
<211> LENGTH: 98
<212> TYPE: PRT
<213> ORGANISM: Artificial
<220> FEATURE:
<223> OTHER INFORMATION: SUMO

<400> SEQUENCE: 40

```
Gly Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Ala Pro Glu Asp
65                  70                  75                  80

Leu Asp Met Glu Asp Asn Asp Ile Ile Glu Ala His Arg Glu Gln Ile
                85                  90                  95

Gly Gly
```

<210> SEQ ID NO 41
<211> LENGTH: 294
<212> TYPE: DNA
<213> ORGANISM: Artificial
<220> FEATURE:
<223> OTHER INFORMATION: SUMO polynucleotide

<400> SEQUENCE: 41

```
ggtagcgata gcgaggtcaa tcaggaagcg aaaccggagg ttaaaccaga ggtgaaaccg    60 gaaaccccaca ttaacttgaa agttagcgat ggtagctccg aaatcttttt caagatcaag   120
aaaaccacgc cgctgcgtcg cctgatggaa gcatttgcca acgtcagggg caaggaaatg   180
gacagcctgc gtttcctgta cgatggcatc cgcattcaag cggaccaagc tccggaggac   240
ctggacatgg aggataacga catcattgag gcccatcgtg agcagattgg tggt          294
```

<210> SEQ ID NO 42
<211> LENGTH: 236
<212> TYPE: PRT
<213> ORGANISM: Artificial
<220> FEATURE:
<223> OTHER INFORMATION: DsbC

<400> SEQUENCE: 42

```
Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45

Thr Val Leu Thr Asn Ser Gly Val Leu Tyr Ile Thr Asp Asp Gly Lys
    50                  55                  60

His Ile Ile Gln Gly Pro Met Tyr Asp Val Ser Gly Thr Ala Pro Val
65                  70                  75                  80
```

```
Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys
225                 230                 235

<210> SEQ ID NO 43
<211> LENGTH: 708
<212> TYPE: DNA
<213> ORGANISM: Artificial
<220> FEATURE:
<223> OTHER INFORMATION: DsbC polynucleotide

<400> SEQUENCE: 43
atgaagaaag gttttatgtt gtttactttg ttagcggcgt tttcaggctt tgctcaggct    60
gatgacgcgg caattcaaca aacgttagcc aaaatgggca tcaaaagcag cgatattcag   120
cccgcgcctg tagctggcat gaagacagtt ctgactaaca gcggcgtgtt gtacatcacc   180
gatgatggta acatatcat tcaggggcca atgtatgacg ttagtggcac ggctccggtc    240
aatgtcacca ataagatgct gttaaagcag ttgaatgcgc ttgaaaaaga gatgatcgtt   300
tataaagcgc cgcaggaaaa acacgtcatc accgtgttta ctgatattac ctgtggttac   360
tgccacaaac tgcatgagca atggcagac tacaacgcgc tggggatcac cgtgcgttat    420
cttgctttcc cgcgccaggg gctggacagc gatgcagaga agaaaatgaa agctatctgg   480
tgtgcgaaag ataaaaacaa agcgtttgat gatgtgatgg caggtaaaag cgtcgcacca   540
gccagttgcg acgtggatat tgccgaccat tacgcacttg gcgtccagct tggcgttagc   600
ggtactccgg cagttgtgct gagcaatggc acacttgttc cgggttacca gccgccgaaa   660
gagatgaaag aattcctcga cgaacaccaa aaaatgacca gcggtaaa               708

<210> SEQ ID NO 44
<211> LENGTH: 58
<212> TYPE: PRT
<213> ORGANISM: Artificial
<220> FEATURE:
<223> OTHER INFORMATION: Z

<400> SEQUENCE: 44

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30
```

```
Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 45
<211> LENGTH: 174
<212> TYPE: DNA
<213> ORGANISM: Artificial
<220> FEATURE:
<223> OTHER INFORMATION: Z polynucleotide

<400> SEQUENCE: 45
gttgataaca agttcaacaa ggaacagcaa aacgcattct atgaaattct gcatctgccg      60
aacctgaatg aagaacagcg taatgcgttt atccaaagcc tgaaagatga cccgagtcaa     120
agcgcaaatc tgctggctga agcgaaaaaa ctgaatgatg cacaggcacc gaaa           174

<210> SEQ ID NO 46
<211> LENGTH: 56
<212> TYPE: PRT
<213> ORGANISM: Artificial
<220> FEATURE:
<223> OTHER INFORMATION: GB1

<400> SEQUENCE: 46

Met Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 47
<211> LENGTH: 168
<212> TYPE: DNA
<213> ORGANISM: Artificial
<220> FEATURE:
<223> OTHER INFORMATION: GB1 polynucleotide

<400> SEQUENCE: 47
atgacctaca aactgattct gaacggcaaa accctgaaag gcgaaacgac gacggaagcg      60
gtggatgcgg cgacggctga aaaagtgttt aaacagtatg cgaacgataa tggcgtcgac     120
ggtgaatgga cctacgatga cgccaccaag acgttcaccg tgacggaa                  168
```

METHODS FOR PRODUCTION AND PURIFICATION OF POLYPEPTIDES

TECHNICAL FIELD

The present invention relates to the field of genetic engineering. More particularly, the present invention relates to a fusion protein comprising a solubility-enhancing peptide tag moiety, a self-aggregating peptide moiety and a target polypeptide moiety and to a method for production and purification of target polypeptides through expressing said fusion protein.

BACKGROUND

Polypeptides have been widely used in the field of medicine and pharmaceutics such as in the development of antitumor drugs, cardiovascular drugs, vaccines, anti-virus drugs, diagnostic kits and the like (Leader et. al, 2008). However, the production of polypeptides remains a bottleneck for the rapidly increasing market requirements. Solid-phase chemical synthesis is a conventional method for polypeptide production. However, if the polypeptide to be produced has more than 30 amino acids, the cost and difficulty for synthesis increase significantly (Bray et al., 2003).

Another efficient strategy is to produce polypeptides recombinantly in a host cell, such as *Escherichia coli* (*E. coli*). *E. coli* expression system has many advantages, such as fast-growing, high expression level and low costs for production. By using the *E. coli* system, one can conveniently obtain desired target polypeptides by introducing an exogenous gene which can be further manipulated to introduce modifications in the encoded amino acid sequence. This method is convenient and easy to scale up. More than 30% of the recombinant therapeutic polypeptides currently available on the market are produced using *E. coli* (Kamionka et. al, 2011; Demain et. al, 2009; Walsh, 2003 and 2006). However, polypeptides less than 100 amino acids in length tend to be degraded by endogenous proteases, which results in a significant reduction in the yields (Murby et. al, 1996; Kuliopulo et. al, 1994; Hannig t. al, 1998).

Protein purification is a key step for the recombinant peptide production methods. It is reported that the cost for isolation and purification covers about 60-80% of the total cost for the production of recombinant polypeptides (Chen Hao et. al, 2002). The conventional methods for purification of recombinant polypeptides include ion exchange chromatography, hydrophobic interaction chromatography, affinity chromatography, and the like. Ion exchange chromatography and hydrophobic interaction chromatography have some special requirements for the starting samples, which largely limits their use. The affinity chromatography may typically result in a high yield of up to 90%, which makes it the most popular method for purification of recombinant proteins. Conventional affinity chromatography techniques involve the fusion expression with a His-tag or a Glutathione transferase tag (GST-tag), which provides a universal means for production of various target polypeptides. However, the affinity columns are expensive and thus limit the applications of affinity chromatography techniques in the industry.

There is still a need of cost-efficient and convenient methods for production and purification of polypeptides.

BRIEF DESCRIPTION

The present invention provides a method for production and purification of polypeptides in a cost-efficient and convenient way, which is based on the use of self-aggregating peptides and solubility-enhancing peptide tags.

In one aspect, the present invention provides a fusion protein comprising a solubility-enhancing peptide tag moiety, a self-aggregating peptide moiety and a target polypeptide moiety, wherein said target polypeptide moiety is located between said solubility-enhancing peptide tag moiety and said self-aggregating peptide moiety, and said target polypeptide moiety is attached to said self-aggregating peptide moiety through a first linker comprising a first cleavage site, wherein said fusion proteins, upon expression in a host cell, are capable of forming active aggregates through the self-aggregating peptide moiety. In some embodiments, said self-aggregating peptide moiety is located at the C-terminal of said fusion protein.

In some embodiments, said self-aggregating peptide moiety comprises an amphipathic self-assembling short peptide. In some embodiments, said amphipathic self-assembling short peptide is selected from the group consisting of an amphipathic β-sheet short peptide, an amphipathic α-helix short peptide and a surfactant-like short peptide.

In some embodiments, said amphipathic β-sheet short peptide is 4-30 amino acid residues in length. In some embodiments, 40%-80% amino acid residues in said amphipathic β-sheet short peptide are hydrophobic amino acids. In a specific embodiment, said amphipathic β-sheet short peptide comprises the amino acid sequence as set forth in SEQ ID NO:1. In some embodiments, the self-aggregating peptide moiety in the fusion protein of the invention comprises one amphipathic β-sheet short peptide. In some embodiments, the self-aggregating peptide moiety in the fusion protein of the invention comprises a tandem repeat of two or more of said amphipathic β-sheet short peptides.

In some embodiments, said amphipathic α-helix short peptide is 4-30 amino acid residues in length. In some embodiments, 40%-80% amino acid residues in said amphipathic α-helix short peptide are hydrophobic amino acids. In a specific embodiment, said amphipathic α-helix short peptide comprises the amino acid sequence as set forth in SEQ ID NO:2. In some embodiments, the self-aggregating peptide moiety in the fusion protein of the invention comprises one amphipathic α-helix short peptide. In some embodiments, the self-aggregating peptide moiety in the fusion protein of the invention comprises a tandem repeat of two or more of said amphipathic α-helix short peptides.

In some embodiments, said surfactant-like short peptide is 7-30 amino acid residues in length and comprises an amino acid sequence represented by the following general formula from N-terminal to C-terminal:

A-B or B-A wherein A is a peptide consisting of hydrophilic amino acid residues, said hydrophilic amino acid residues may be the same or different, and are selected from the group consisting of Lys, Asp, Arg, Glu, His, Ser, Thr, Asn and Gln; B is a peptide consisting of hydrophobic amino acid residues, said hydrophobic amino acid residues may be the same or different, and are selected from the group consisting of Leu, Gly, Ala, Val, Ile, Phe and Trp; A and B are linked by a peptide bond; and the proportion of hydrophobic amino acid residues in said surfactant-like short peptide is 55%-95%. In some embodiments, said surfactant-like short peptide is 8 amino acid residues in length, wherein the proportion of hydrophobic amino acid residues is 75%. In some specific embodiments, said surfactant-like short peptide consists of an amino acid sequence as set forth in SEQ ID NO:3, SEQ ID NO:4 or SEQ ID NO:5.

In some specific embodiments, said solubility-enhancing peptide tag in the fusion protein of the invention is selected from the group consisting of NusA, GST, Trx, SUMO, DsbC, Z, GB1, MBP and T7PK.

In some embodiments, said first cleavage site in the fusion protein of the invention is selected from the group consisting of a chemical cleavage site, an enzymatic cleavage site and a self-cleavage site. In some embodiments, said self-cleavage site comprises an intein. In some specific embodiments, said intein is Mxe GyrA having the sequence as set forth in SEQ ID NO:6. In some specific embodiments, said Mxe GyrA is directly attached to the C-terminal of said target polypeptide.

In some alternative embodiments, said first linker in the fusion protein of the invention further comprises a spacer.

In some embodiments, said target polypeptide in the fusion protein of the invention is attached to said solubility-enhancing peptide tag through a second linker. In some alternative embodiments, said second linker comprises a spacer. In some other alternative embodiments, said second linker comprises a second cleavage site, wherein the cleavage condition for said second cleavage site is different from that for said first cleavage site. In some embodiments, said second cleavage site is selected from the group consisting of a second chemical cleavage site, a second enzymatic cleavage site and a second self-cleavage site. In some specific embodiments, said second enzymatic cleavage site comprises an Enterokinase recognition sequence as set forth in SEQ ID NO:7. In some specific embodiments, said Enterokinase recognition sequence is directly attached to the N-terminal of said target polypeptide. In some alternative embodiments, said second linker comprises a spacer in addition to the second cleavage site.

In some embodiments, said target polypeptide in the fusion protein of the invention is a polypeptide of 30-100 amino acid residues in length.

In another aspect, the present invention provides a polynucleotide comprising a nucleotide sequence encoding the above said fusion protein of the invention, or the complement thereof.

In still another aspect, the present invention provides an expression construct comprising the polynucleotide of the invention.

In still another aspect, the present invention provides a host cell which comprises the polynucleotide of the invention or has been transformed with the expression construct of the invention, wherein said host cell is capable of expressing the fusion protein of the invention.

In still another aspect, the present invention provides a method for production and purification of a target polypeptide, said method comprises the steps of:

(a) culturing the host cell of the invention so as to express the fusion protein of the invention;

(b) lysing said host cells, then removing the soluble portion of the cell lysate and collecting the insoluble portion;

(c) releasing the soluble target polypeptide with the solubility-enhancing peptide tag from said insoluble portion by cleaving the first cleavage site; and (d) removing the insoluble portion formed in step (c) and recovering the soluble portion containing said target polypeptide.

In some embodiments, the methods of the invention for production and purification of a target polypeptide further comprises:

(e) if a second cleavage site is present in the expressed fusion protein, cleaving said second cleavage site so as to separate said target poly peptide from said solubility-enhancing peptide tag;

(f) removing said solubility-enhancing peptide tag and collecting the purified target polypeptide.

BRIEF DESCRIPTIONS OF THE DRAWINGS

FIG. 1 shows the strategy for polypeptide production and purification based on a self-aggregating peptide (ELK16) and a solubility-enhancing peptide tag (Trx), and the schematic diagram of the expression vectors. A: with a solubility-enhancing peptide tag; B: without a solubility-enhancing peptide tag; C: pET-LipA-Intein-ELK16; and D: pET-Trx-EK-Intein-ELK16.

FIG. 2 shows the results of target polypeptide expression and purification. A: without a Trx tag; B: with a Trx tag.

DETAILED DESCRIPTION OF THE INVENTION

Figure 1:
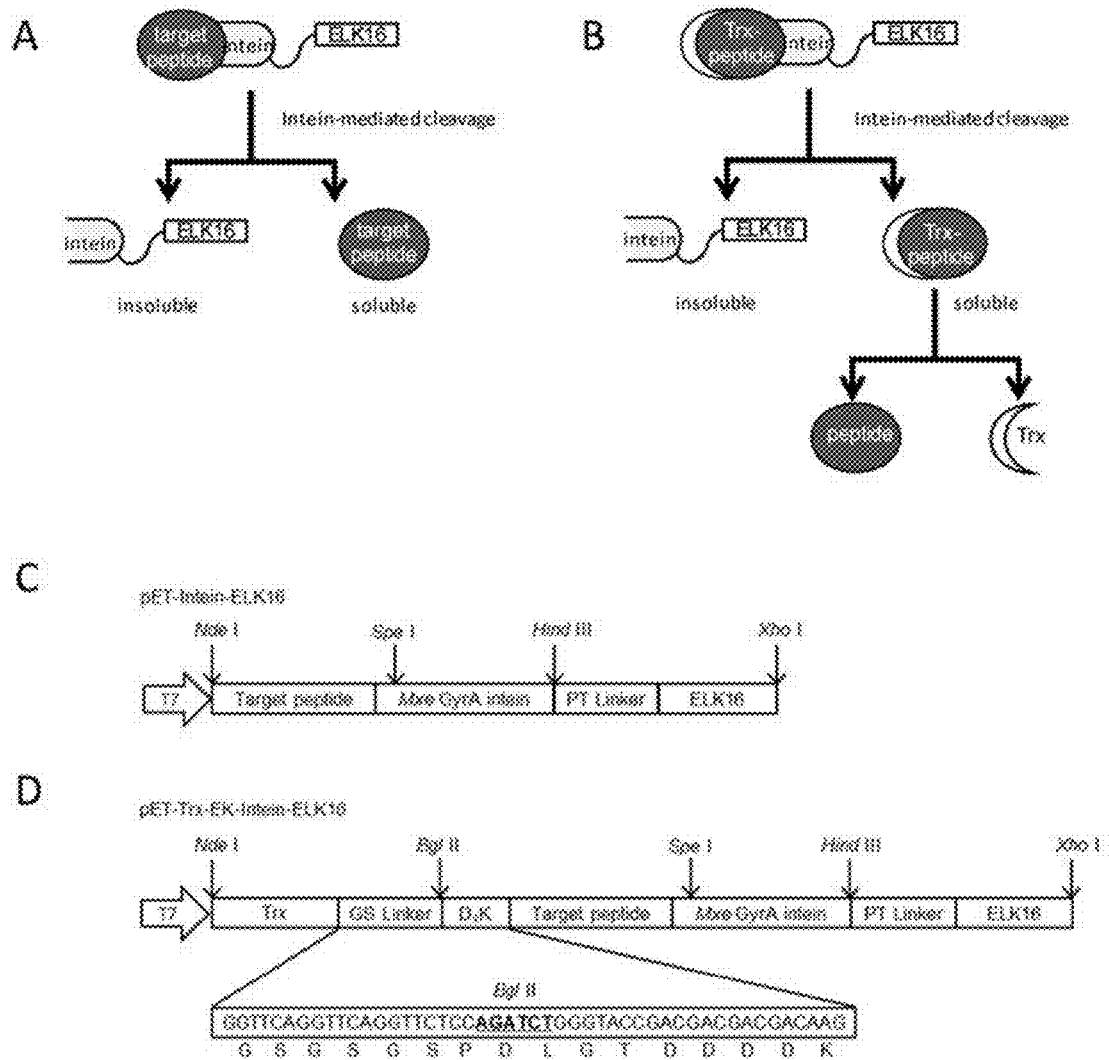

In a first aspect, the present invention provides a fusion protein comprising a solubility-enhancing peptide tag moiety, a self-aggregating peptide moiety and a target polypeptide moiety, wherein said target polypeptide moiety is located between said solubility-enhancing peptide tag moiety and said self-aggregating peptide moiety, and said target polypeptide moiety is attached to said self-aggregating peptide moiety through a first linker comprising a first cleavage site, wherein said fusion proteins, upon expression in a host cell, are capable of forming active aggregates through the self-aggregating peptide moiety.

In a second aspect, the present invention provides a polynucleotide which comprises a nucleotide sequence encoding the fusion protein of the invention, or the complement thereof.

In a third aspect, the present invention provides an expression construct which comprises the polynucleotide of the invention.

In a fourth aspect, the present invention provides a host cell which comprises the polynucleotide of the invention or has been transformed with the expression construct of the invention, wherein said host cell is capable of expressing the fusion protein of the invention.

In a fifth aspect, the present invention provides a method for production and purification of a target polypeptide, said method comprises the steps of: (a) culturing the host cells of the invention and thereby expressing the fusion protein of the invention; (b) lysing said host cells, then removing the soluble portion of the cell lysate and collecting the insoluble portion; (c) releasing the soluble target polypeptide with the solubility-enhancing peptide tag from said insoluble portion by cleaving the first cleavage site; and (d) removing the insoluble portion formed in step (c) and recovering the soluble portion containing said target polypeptide.

As used herein, the terms "polypeptide" and "protein" are used interchangeably and defined as a biological molecule composed of amino acid residues linked by peptide bonds. As used herein, "target polypeptide" or "target protein" refers to any polypeptide or protein that can be produced and purified through the methods of the invention. Non-limiting examples include enzymes, hormones, chains of immunoglobulin, therapeutic polypeptides such as anti-cancer polypeptides, diagnostic polypeptides, polypeptides for the purpose of immunization, and biological active fragments thereof. The target polypeptide may be from any sources, including polypeptides of microorganism origin, polypeptides of mammalian origin, artificial proteins (such as fusion proteins or mutated proteins), and the like.

The target polypeptide or protein may be of any length. The target polypeptide that can be produced and purified through the methods of the invention may be 20-200, 25-150, 30-120, 30-100 amino acid residues in length, for example, about 30, about 40, about 50, about 60, about 70, about 80, or about 90 amino acid residues in length.

The examples of polypeptides that can be produced and purified by the methods of the invention include, but not limit to, glucagon-like peptide (GLP-1), B-type natriuretic peptide (BNP), Exendin (Ex-4), chemokine CCL5, stromal cell derived factor-1 alpha (SDF-1a), insulin-like growth factor-1 alpha (IGF-1α), Leptin (Lep), Calcitonin, Sermorelin, Thymosin, Lepirudin, Cecropin, Histatin, defensin, and Kringle 1-5, or biological active fragments thereof.

As used herein, "solubility-enhancing peptide tag" refers to a fusion tag that, upon fusion with a target polypeptide, can facilitate the folding of the target polypeptide and increase the solubility of the fusion protein. Various "solubility-enhancing peptide tags" are well known in the art. Suitable solubility-enhancing peptide tags that can be used in the invention include, but not limit to, NusA, GST, Trx, SUMO, DsbC, Z, GB1, MBP and T7PK (Leder et al., 2007; Esposito and Chatterjee, 2006; Waugh, 2005). In a preferred embodiment, said solubility-enhancing peptide tag is Trx.

As used herein, "self-aggregating peptide" refers to a polypeptide that, upon fusion with a target polypeptide moiety and expression as a fusion protein in a host cell, can mediate the formation of insoluble active aggregates from the fusion proteins. As used herein, "active aggregate" means that the target polypeptide moiety in the aggregate can fold correctly and maintain its activity, or the target polypeptide moiety is soluble after being separated from the self-aggregating peptide.

Not intended to be limited within any theory, it is known in the art that some amphipathic polypeptides are capable of spontaneously forming a specific self-assembling structure through hydrophobic interaction and other driving forces, because they have separate hydrophilic and hydrophobic regions (Zhao et al., 2008). Surprisingly, the inventors found that some amphipathic short peptides with self-assembling ability can induce the formation of active aggregates in cells. The amphipathic self-assembling short peptide used as the self-aggregating peptide of the invention may be selected from the group consisting of an amphipathic β-sheet short peptide, an amphipathic α-helix short peptide and a surfactant-like short peptide.

As used herein, "amphipathic β-sheet short peptide" refers to a short peptide of 4-30 amino acid residues, composed of alternatively arranged hydrophobic amino acids and charged hydrophilic amino acids, and when forming a β-sheet, the hydrophobic amino acid residues are present on one side and the alternatively arranged positive-charged and negative-charged hydrophilic amino acid residues are present on the other side. Such peptides may form self-assembling structures through the action of hydrophobic interaction, electrostatic interaction and hydrogen bonding. Generally, the longer the amphipathic β-sheet structure is or the stronger hydrophobicity it has, the higher tendency of the occurrence of the self-assembling and the stronger mechanic strength of the formed aggregates. To ensure sufficient self-assembling ability, the amphipathic β-sheet short peptide of the invention should comprise certain amount of hydrophobic amino acid residues. The amphipathic β-sheet short peptide of the invention may comprise 40-80%, 45-70%, 50-60%, such as about 50% hydrophobic amino acid residues. A specific example of the amphipathic β-sheet short peptides useful in the invention is ELK16 (having the amino acid sequence as set forth in SEQ ID NO:1: LELELKLKLELELKLK).

Polypeptides with self-assembling properties which are formed by tandem arrangement of a plurality of repeat units have been reported, such as elastin-like protein (ELP) consisting of 110 VPGXG repeat units, the assembling properties of which depends on the number of the repeat units (Banki, et al., 2005; MacEwan and Chilkoti, 2010). It has also been reported that the self-assembling tendency of amphipathic β-sheet that comprises multiple repeat units increases as the number of repeat units increases (Zhang et al., 1992). It is expected that a polypeptide comprising a plurality of above-mentioned "amphipathic β-sheet short peptides" arranged in a tandem repeat manner may retain or even obtain enhanced self-assembling ability.

Therefore, the self-aggregating peptide moiety according to the present invention may comprise one or more (tandem repeats) of said amphipathic β-sheet short peptide. The self-aggregating peptide moiety according to the present invention may comprise 1-150, 1-130, 1-110, 1-90, 1-70, 1-50, 1-30, 1-10, 1-5, for example, 1, 2, 3, 4 or 5 of said amphipathic β-sheet short peptides. Two or more of said amphipathic β-sheet short peptides may be linked tandemly in the self-aggregating peptide moiety. But for the convenience of recombinant manipulation and in consideration of the cost, it is expected to use less repeats. Thus, in some embodiments, said "self-aggregating peptide moiety" only includes one amphipathic β-sheet short peptide.

The α-helix is a secondary protein structure in which the backbone of a peptide chain extends around an axis in a spiral manner. As used herein, "amphipathic α-helix short peptide" refers to a short peptide of 4-30 amino acid residues, which has a unique arrangement of hydrophilic and hydrophobic amino acids compared with typical α-helix that makes one side of said α-helix mainly composed of hydrophilic amino acids, while the other side mainly composed of hydrophobic amino acids. It is believed that such amphipathic α-helices will assemble spontaneously in aqueous solution by forming coiled-coils. Two α-helices bind to each other through hydrophobic interaction, and such binding is stabilized by the electrostatic interaction between charged amino acids. The amphipathic α-helix short peptide of the invention may comprise 40-80%, 45-70%, 50-60%, such as about 50% hydrophobic amino acid residues. A specific example of the amphipathic α-helix short peptides useful in the invention is 18A (having the amino acid sequence as set forth in SEQ ID NO:2: EWLKAFYEKVLEKLKELF).

Similar to the amphipathic β-sheet, a polypeptide composed of tandem repeats of said amphipathic α-helix short peptides may retain or even obtain enhanced self-assembling ability. Therefore, the self-aggregating peptide moiety according to the present invention may comprise one or more (tandem repeats) of said amphipathic α-helix short peptides. The self-aggregating peptide moiety according to the present invention may comprise 1-150, 1-130, 1-110, 1-90, 1-70, 1-50, 1-30, 1-10, 1-5, for example, 1, 2, 3, 4 or 5 of said amphipathic α-helix short peptides. Two or more of said amphipathic α-helix short peptides may be linked tandemly in the self-aggregating peptide moiety. For the convenience of recombinant manipulation and in consideration of the cost, it is expected to use less repeats. Thus, in some embodiments, the "self-aggregating peptide moiety" according to the present invention only includes one amphipathic α-helix short peptide.

"Surfactant-like peptide" is another type of amphipathic peptides that may be used as the self-aggregating peptide of the invention. Surfactant-like peptides are typically composed of 7-30 amino acid residues, having a physical length of about 2-5 nm and having a structure similar to lipid that is formed by a tail of hydrophobic amino acids and a head of hydrophilic amino acids. Surfactant-like structures have similar properties with surfactants and can form assembling structures such as micelles, nanotubes and the like in aqueous solution. The surfactant-like short peptides suitable to be used as the self-aggregating peptide of the invention may be 7-30 amino acids in length and comprise an amino acid sequence represented by the following general formula from N-terminal to C-terminal:

A-B or B-A,

In the above formula, A and B are linked by a peptide bond. A is a hydrophilic head consisting of hydrophilic amino acid residues, which may be same or different and are selected from the group consisting of Lys, Asp, Arg, Glu, His, Ser, Thr, Asn and Gln. The example of A includes KD, KK, and the like. B is a hydrophobic tail consisting of hydrophobic amino acids, which may be same or different and are selected from the group consisting of Leu, Gly, Ala, Val, Ile, Phe and Trp. The example of B includes LLLLLL (L6), GAVIL, and the like. The proportion of hydrophobic amino acids in a surfactant-like short peptide according to the present invention is higher than that of the hydrophilic amino acids. The proportion of hydrophobic amino acids in the surfactant-like short peptide may be 55-95%, 60-95%, 65-95%, 70-95%, 75-95%, 80-95%, 85-95%, and 90-95%. In some embodiments, said surfactant-like short peptide is 8 amino acid residues in length, wherein the proportion of hydrophobic amino acid residues is 75%. Specific examples of the surfactant-like short peptide suitable to be used as the self-aggregating peptide of the invention include L6KD, L6K2 or DKL6, the amino acid sequences of which are set forth in SEQ ID NO:3, SEQ ID NO:4 or SEQ ID NO:5, respectively.

In addition, it has been reported that some protein domains, such as β-amyloid, VP1, MalE31, $CBD_{clos}$ and the like, can also mediate the fusion proteins to form aggregates. It is expected that such domains can also be used as the "self-aggregating peptide" of the present invention. However, the structures of these protein domains are relatively complicated and the mechanisms for inducing aggregation are still unclear (Mitraki, 2010). It is preferred to use amphipathic self-assembling short peptides which are relatively short and simple in structure.

In a previous study by the inventors, it was found that, when a self-aggregating peptide having the ability to induce the formation of active aggregates (such as an amphipathic self-assembling short peptide) is fused to a target polypeptide and expressed as a fusion protein in a host cell, the expressed fusion proteins can form insoluble aggregates. The formation of aggregates can avoid the degradation of said fusion protein by endoproteinases, and thus the yield of the target polypeptide can be increased. After the lysis of the cells, insoluble aggregates can be harvested from cell lysate simply by centrifugation or filtration. The soluble impurities are removed, resulting in the rough purification of the fusion protein. Then, by cleaving the cleavage site within the linker between the self-aggregating peptide moiety and the target polypeptide, the soluble portion containing the target polypeptide is released from the insoluble portion (precipitates) and distributed into the suspension. Through simple centrifugation or filtration, the insoluble impurities can be removed, and the soluble target polypeptide can be harvested. Such a self-aggregating peptide based method for production of polypeptides (the schematic diagram is shown in FIG. 1 A) can simplify the procedures for isolation and purification, avoid the use of expensive column purification, and significantly reduce the cost.

It is well known in the art that a solubility-enhancing peptide tag can increase the solubility of a fusion protein, which is contrary to the effect of self-aggregating peptides that tend to make the fusion protein insoluble. Surprisingly, the inventors have found that a fusion protein comprising a solubility-enhancing peptide tag moiety, a target polypeptide moiety and a self-aggregating peptide moiety, when expressed in a host cell, still forms insoluble aggregates and can be isolated and purified by the above procedures (the schematic diagram is shown in FIG. 1B). The solubility-enhancing peptide tag can further facilitate the correct folding of the target polypeptide and can maintain or enhance the solubility of the target polypeptide after the removal of the self-aggregating peptide moiety. Not intended to be limited by any theories, it is assumed that this is because of some kind of functional balance between the solubility-enhancing peptide tag and the self-aggregating peptide. In addition, the inventors also found that the solubility-enhancing peptide tag may improve the expression of the fusion protein, and thus it may be used to produce some polypeptides that were considered as difficult to produce with existing recombinant methods.

According to the present invention, the target polypeptide is attached to said self-aggregating peptide moiety through a first linker, wherein said first linker comprises a first cleavage site. As used herein, "cleavage site" comprises a sequence that is required for cleavage, such as protease recognition sequence, intein sequence for self-cleavage, and the like.

The first cleavage site according to the invention for releasing the target polypeptide containing soluble portion from the insoluble portion (precipitates) may comprise a chemical cleavage site, an enzymatic cleavage site, a self-cleavage site, or any other cleavage sites that are known in the art. A preferred first cleavage site of the invention is a self-cleavage site. For example, the first cleavage site comprises an amino acid sequence of intein that is self-cleavable. This is because the intein-based cleavage does not require the addition of enzymes or harmful substances used in chemical cleavage methods. The cleavage can be induced by simply changing the buffer conditions for the aggregates (Wu et al., 1998; TELENTI et al., 1997). Various self-cleavable inteins are known in the art, such as a series of inteins with different self-cleavage properties available from NEB. In a specific embodiment, said intein is Mxe GyrA having the sequence as set forth in SEQ ID NO:6. Addition of suitable amount of dithiothreitol (DTT) into the buffer system can induce self-cleavage at the carboxyl terminal of this intein.

The target polypeptide in the fusion protein of the invention can be attached to the solubility-enhancing peptide tag directly, or can be attached to the solubility-enhancing peptide tag through a second linker. If it is desired to obtain target polypeptide without a tag, a second cleavage site can be introduced into said second linker. After the first cleavage step to separate the target polypeptide from the self-aggregating peptide moiety, the target polypeptide is separated from the solubility-enhancing peptide tag by cleaving said second cleavage site; and then the target polypeptide without a tag can be obtained through an additional purification step (e.g., purification by HPLC). Therefore, the method for production and purification of a target polypeptide according to the present invention may further comprises: (e) if a second cleavage site is present, cleaving said second cleavage site so as to separate said target polypeptide from said solubility-enhancing peptide tag; and (f) removing said solubility-enhancing peptide tag and collecting the purified target polypeptide.

The second cleavage site according to the invention for separating the target polypeptide from the solubility-enhancing peptide tag comprises a chemical cleavage site, an enzymatic cleavage site, a self-cleavage site, or any other cleavage sites that are known in the art. In some embodiments, said second cleavage site is an enzymatic cleavage site. In some specific embodiments, said enzymatic cleavage site comprises the Enterokinase recognition site (amino acid sequence: DDDDK, SEQ ID NO:7).

It should be understood that said second cleavage site should have a cleavage condition different from that of the first cleavage site so as to avoid the cleavage of the second cleavage site when cleaving the first cleavage site, thus maintaining the attachment of the target polypeptide and the solubility-enhancing peptide tag. This can be achieved by various means. The non-limiting examples include, for example, the first cleavage site is self-cleavable while the second cleavage site is cleaved by is enzymatic methods, or both the first and second cleavage sites are cleaved by enzymatic methods but they are cleaved by different enzymes.

It can be understood by one skilled in the art that spacers may be used to link different parts of the fusion protein so as to reduce the interference between different parts of the fusion protein of the invention. As used herein, a "spacer" refers to a polypeptide having a certain length and composed of amino acids with low hydrophobicity and low charge effect, with the aid of which each part of the fusion protein can be extended sufficiently and fold into their respective nature confirmation without interfering with each other. Thus, besides the cleavage sites, said first linker and/or second linker may additionally comprises a spacer. In some embodiments, if it is unnecessary to remove the solubility-enhancing peptide tag, the second linker in the fusion protein of the invention may comprise a spacer only and do not have a cleavage site.

Such spacers commonly used in the art include, for example, flexible GS-type spacer rich in glycine (G) and serine (G), rigid PT-type spacer rich in proline (P) and Threonine (T). It is preferred to use the PT-type spacer in the present invention since the PT-type spacer has better tolerance to proteases as compared with the GS-type spacer. In some specific embodiments, the spacer used in the invention is a PT-type spacer with the sequence of PTPPTTPTPPTTPTPT (SEQ ID NO:8).

In the production of polypeptide therapeutics, it is usually required that the recombinant produced polypeptide has the exact sequence as the desired target polypeptide, i.e., without additional amino acid residues at either end of the polypeptide. According to the present invention, this can be achieved by choosing suitable first and second cleavage sites and choosing their suitable linking manner with the target polypeptide. One skilled in the art will be aware of how to make such choices according to the properties of specific cleavage sites. For example, in one specific embodiment, Mxe GyrA intein of the first cleavage site may be attached to the C-terminal of the target polypeptide directly, so that there is no additional amino acid residue between Mxe GyrA and the target polypeptide. Since Mxe GyrA directly cleaves at its N-terminal, the C-terminal of the polypeptide obtained after such cleavage will have no additional amino acid residues. In another specific embodiment, Enterokinase recognition site of the second cleavage site may be attached to the N-terminal of the target polypeptide directly, so that there is no additional amino acid residue between the Enterokinase recognition site and the target polypeptide. Since Enterokinase directly cleaves at the C-terminal of its recognition site, the N-terminal of the polypeptide obtained after such cleavage will have no additional amino acid residues. If it is desired to obtain a target polypeptide without any additional amino acid residues at either ends, Mxe GyrA of the first cleavage site may be attached to the C-terminal of the target polypeptide directly while Enterokinase recognition site of the second cleavage site may be attached to the N-terminal of the target polypeptide directly.

As mentioned above, the present invention also relates to a polynucleotide which comprises a nucleotide sequence encoding the fusion protein of the invention or the complement thereof. As used herein, a "polynucleotide" refers to a macromolecule formed by a plurality of nucleotides linked through 3'-5'-phosphodiester bonds. Said nucleotide includes ribonucleotide or deoxyribonucleotide. The sequence of the polynucleotide according to the invention may be codon-optimized for different host cells (e.g., E. coli) so as to improve the expression of the fusion protein. The methods for codon-optimization are well known in the art.

As mentioned above, the present invention also relates to an expression construct comprising the above polynucleotide of the invention. In the expression construct of the invention, the sequence of polynucleotide encoding said fusion protein is operably linked to is expression control sequences so as to obtain the desired transcription and produce said fusion protein in the host cells eventually. Suitable expression control sequences include, but not limit to, promoter, enhancer, ribosome action site such as ribosome binding site, polyadenylation site, transcription splicing sequence, transcription terminator, sequences that stabilizing mRNA, and the like.

The vectors used for the expression constructs of the invention include the vectors that autonomously replicate in host cells, such as plasmid vectors, and the vectors that can integrate into the DNA of host cells and replicate with the DNA of host cells. Various vectors suitable for the invention are commercially available. In one specific embodiment, the expression construct of the invention is derived from pET30a (+) (Novagen).

The present invention also provides a host cell which comprises the polynucleotide of the invention or has been transformed with the expression construct of the invention, wherein said host cell is capable of expressing the fusion protein of the invention. The host cells used for the expression of the fusion protein of the invention include prokaryote cells, yeast cells and higher eukaryote cells. The exemplary prokaryote host includes bacteria from *Escherichia, Bacillus, Salmonella, Pseudomonas* and *Streptomyces*. In preferred embodiments, the host cells are *Escherichia* cells, preferably *E. coli* cells. In one specific embodiment of the invention, the host cells are *E. coli* BL21 (DE3) strain cells (Novagen).

The recombinant expression construct of the invention can be introduced into host cells by various techniques well known in the art. Said techniques include, but not limit to, heat shock transformation, electroporation, DEAE-glucan transfection, microinjection, liposome-mediated transfection, calcium phosphate precipitation, protoplast fusion, microparticle bombardment, viral transformation and similar techniques.

In the methods of the invention for production and purification of target polypeptide as described above, the problem that polypeptides of medium length tend to be degraded in recombinant production is solved by forming insoluble aggregates which protect the target polypeptides; the expression of target polypeptides is improved by using the solubility-enhancing peptide tag; the simplified purification is achieved and use of expensive isolation columns is avoided through the self-aggregating and self-cleavage of the fusion protein. Therefore, the method of the invention is a low-cost, convenient and efficient method for production and purification of polypeptides.

EXAMPLES

This invention is further illustrated by the following examples which should not be construed as limiting.

Example 1

Construction of ELK16 Fusion Expression Vector

Figure 10:
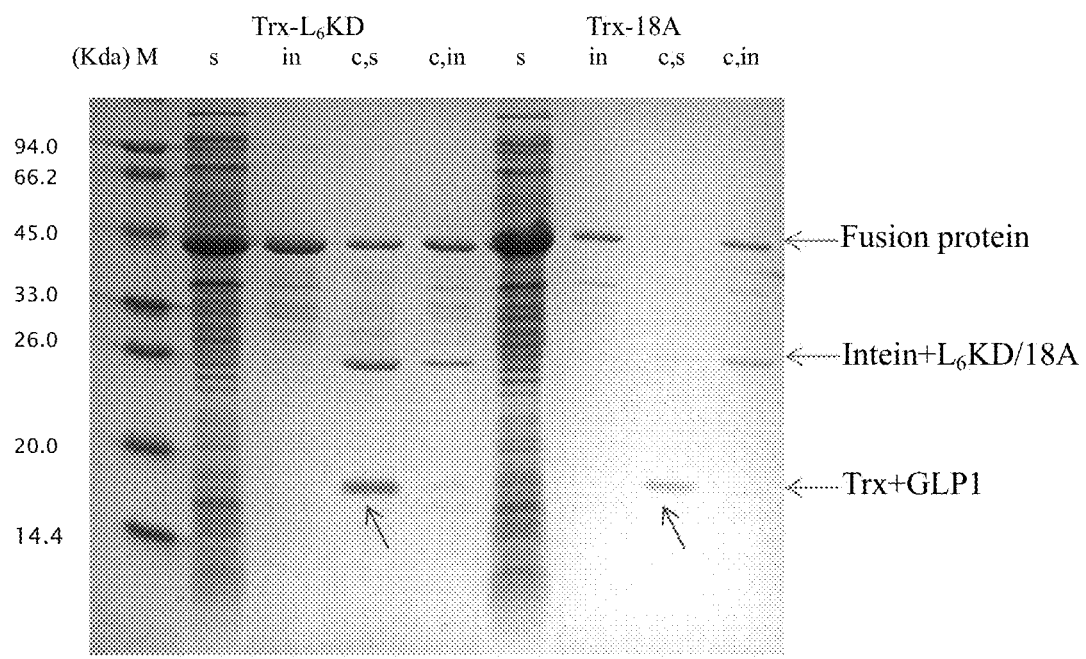
FIG. 10 shows the results of GLP-1 expression and purification with the combination of self-aggregating peptide 18A or L6KD and solubility-enhancing peptide tag Trx.

The expression vectors pET-LipA-Intein-ELK16 and pET-Trx-EK-Intein-ELK16 used in the Examples were constructed as follows:

First, the vector pET-LipA-Intein-ELK16 was constructed. Its structure is shown in FIG. 10. The sequence of the "target peptide" in said vector is the sequence of Bacillus subtilis lipase A (LipA).

The commercial pET-30a(+) plasmid vector from Novogen was used. The nucleotide sequences of PT-type spacer and ELK16 were designed using the online DNAworks. A polynucleotide comprising the nucleotide sequences encoding Bacillus subtilis LipA, the PT-type spacer and ELK16 was synthesized by overlapping PCR with LipA at the N-terminal. This polynucleotide was then inserted into pET-30a(+) between NdeI and XhoI so as to form pET-30a(+)-LipA-ELK16.

The pET-30a(+)-LipA-ELK16 plasmid and pTWIN1 plasmid (New England Biolab) were extracted using the Pure-Plasmid Mini Kits (Tiangen Inc). The polynucleotide fragment of LipA and the polynucleotide fragment of intein Mxe GyrA were amplified using conventional PCR with the following two set of primers, respectively.

The first set of primers: upstream primer 5'-GCGATA<u>CATATG</u>CACCATCACCATCA-3 (SEQ ID NO:9, the underlined is the recognition site of NdeI) and downstream primer 5'-GCATCTCCCGTGATGCACATTCGCATATTCGTATTCTGGCCCC-3' (SEQ ID NO:10). The second set of primers: upstream primer 5'-GGGGCCAGAATAC-GAATATGCGAATGTGCATCACGGGAGAT-3' (SEQ ID NO:11) and downstream primer 5'-ATTTTA<u>AAGCTT</u>AGCGTGGCTGACGAACCCGTTC-3' (SEQ ID NO: 12, the underlined is the recognition site of Hind III).

Pfu polymerase (Tiangen Inc) was used in the PCR reaction. The PCR was run according to the following program: 94° C. 2 min; then 94° C. 1 min, 57° C. 1 min, 72° C. 40 sec, for 30 cycles; and 72° C. 10 min. After amplification, PCR products were analyzed with 1% agarose gel electrophoresis. The result shows that the expected bands were obtained. The two fragments were extracted by agarose gel separation and then used as templates for overlapping PCR. PCR was initially run without primers: 94° C. 2 min; then 94° C. 1 min, 70° C. 1 min, 72° C. 80 sec, for total 10 cycles; and 72° C. 10 min. After an additional incubation at 94° C. for 2 min, the primers 5'-GCGATACATATGCACCATCACCATCA-3' (SEQ ID NO:13) and 5'-ATTTTAAAGCTTAGCGTGGCT-GACGAACCCGTTC-3' (SEQ ID NO:14) were added; and FOR was run according to the program of: 94° C. 1 min, 57° C. 1 min, 72° C. 40 sec, for total 17 cycles; and 72° C. 10 min. After amplification, PCR products were analyzed with 1% agarose gel electrophoresis. The result shows that the expected bands were obtained. The products of overlapping FOR were double-digested with NdeI and HindIII and then inserted into pET-30a(+)-LipA-ELK16 double-digested with the same enzymes. The ligation products were transformed into E. coli BL21 (DE3) competent cells (Novagen). The transformed cells were plated onto LB plates supplemented with 50 µg/mL kanamycin. Plasmid was extracted from positive clones and sequencing results showed that the obtained pET-LipA-intein-ELK16 was correct.

The vector pET-Trx-EK-Intein-ELK16 was also constructed. Its structure is shown in FIG. 1D.

Gene trxA encoding the Trx protein was amplified using primers Trx-For and Trx-Rev in Table 1. Genomic DNA of E. coli strain BL21 (DE3) was used as the template. The amplified products were double-digested with NdeI and SpeI and inserted into pET-LipA-Intein-ELK16 double-digested with the same enzymes. The ligation products were transformed into E. coli BL21 (DE3) competent cells, and subsequently the transformed cells were plated onto LB plates supplemented with 50 µg/mL kanamycin. Plasmid was extracted from positive clones and the sequencing results showed that the obtained pET-Trx-Intein-ELK16 was correct.

Next, the intein gene with an EK recognition site was amplified using primers Trx-EK-For and Trx-EK-Rev in Table 1. The plasmid pET-LipA-Intein-ELK16 was used as the template. The amplified products were double-digested with BglII and HindIII and inserted into pET-trx-intein-ELK16 double-digested with the same enzymes. The ligation products were transformed into E. coli BL21 (DE3) competent cells, and subsequently the transformed cells were plated onto LB plates supplemented with 50 µg/mL kanamycin. Plasmid was extracted from positive clones and the sequencing results showed that the obtained pET-Trx-EK-Intein-ELK16 was correct.

TABLE 1

| Primer | Nucleotide sequence | SEQ ID NO | description |
| --- | --- | --- | --- |
| Trx-For | 5'-AGTTA<u>CATATG</u>AGCGATAAAATTATTC-3' | 15 | NdeI |
| Trx-Rev | 5'-TCACG<u>ACTAGT</u>GCATCTCCCGTGATGCACATTCGCAT<u>GAT ATC</u>AGAACCTGAACCTGAACC<u>AGATCT</u>CGCCAGGTTAGCGT CGAGGAAC-3' | 16 | SpeI, EcoRV, BglII |
| Trx-EK-For | 5'-AGTCA<u>AGATCT</u>GGGTACCGACGACGACGACAAGGATATC ATGCGAATGTGCATCACGGGAGATGC-3' | 17 | BglII |
| Trx-EK-Rev | 5'-GTCGG<u>AAGCTT</u>AGCGTGGCTGACGAACCCGTTC-3' | 18 | HindIII |

Example 2

Construction of ELK16 Fusion Expression Constructs for Seven Different Polypeptides GLP-1, BNP, Ex-4, CCL5, SDF-1α, IGF-1α and Lep were selected as the target polypeptides to be produced and purified with the method of the present invention. The information for these polypeptides is listed in Table 2.

TABLE 2

| Target polypeptide | length | Expression in E. coli | Amino acid sequence (SEQ ID NO) | Optimized nucleotide sequence (SEQ ID NO) |
|---|---|---|---|---|
| GLP-1 | 31 aa | Soluble as a fusion, otherwise will be degraded (Wu et al., 2011) | 19 | 20 |
| BNP | 32 aa | Soluble as a fusion, otherwise will be degraded (Sun et. al., 2005) | 21 | 22 |
| Ex-4 | 39 aa | Soluble as a fusion, otherwise will be degraded (Bosse-Doeneck et. al., 2008) | 23 | 24 |
| CCL-5 | 66 aa | Inclusion bodies (Proudfoot et. al., 1995) | 25 | 26 |
| SDF-1α | 67 aa | Inclusion bodies (Cho et. al., 2008) | 27 | 28 |
| IGF-1α | 70 aa | Inclusion bodies (Zhang et. al,, 2010) | 29 | 30 |
| Lep | 146 aa | Inclusion bodies (Gertler et. al., 1998) | 31 | 32 |

The nucleotide sequences encoding the above target polypeptides were codon-optimized (see Table 2) so as to obtain better expression in *E. coli*. The corresponding polynucleotides were obtained through chemical synthesis.

GLP-1 was taken as an example to shown the construction of ELK16 fusion expression constructs for seven different polypeptides.

The primers used for amplifying GLP-1 were listed in Table 3. The polynucleotide encoding GLP-1 was PCR amplified with primers GLP1-F and GLP1-R as shown in Table 3, and the PCR products were digested with NdeI and SpeI and then inserted into the expression vector pET-LipA-Intein-ELK16 as shown in FIG. 10 treated with the same double-digestion between the NdeI site and the SpeI site which is located within the intein encoding sequence in the vector (17 bases from 5' end of the intein encoding sequence). The 5' end sequence of the intein encoding sequence was unchanged. In addition, the polynucleotide encoding the target polypeptide was amplified with primers Trx-GLP1-F and GLP1-R as shown in Table 3, and inserted into pET-Trx-EK-Intein-ELK16 double-digested with BglII and SpeI. Meanwhile, an Enterokinase cleavage site DDDDK (Asp-Asp-Asp-Asp-Lys) was incorporated between BglII and sequence encoding the target polypeptide.

Example 3

Expression and Rough Purification of Seven Different Polypeptides

The fusion expression constructs obtained in Example 2 were transformed in to *E. coli* BL21 (DE3) competent cells through the calcium chloride method. Positive clones were identified by colony PCR and plasmid sequencing.

The positive clones were inoculated into LB medium. Expression was induced with 0.2 mM IPTG at 23° C., 30° C., and 37° C. for 6 hours, respectively. The bacteria cells were collected and the $OD_{600}$ of which were determined (1 OD means the cell amount in 1 mL medium with $OD_{600}$ of 1).

Bacteria cells were resuspended to 20 OD/mL with lysis buffer (2.4 g Tris, 29.22 g NaCl and 0.37 g $Na_2EDTA \cdot {}_2H_2O$, adjusted with water to 1 liter, pH 8.2) and subjected to ultrasonication. After centrifugation at 10000 rpm for 10 min at 4° C., the supernatants and pellets were collected respectively. The pellets were washed once with lysis buffer supplemented with 0.5% Triton X-100 to remove cell membrane debris, and then twice with lysis buffer to substantially remove Triton X-100.

The washed pellets were thoroughly resuspended in an intein cleavage buffer containing 40 mM DTT (0.62 g DTT dissolved in 100 ml lysis buffer, stored at −20° C.), and incubated at 4° C. for 24 h so as to allow sufficient self-cleavage of the intein.

Then, suspension and pellets were separated by centrifugation, and the pellets were resuspended with lysis buffer of the same volume as that used in the last resuspension step.

The aggregates obtained as above and the pellets and supernatants formed after intein-mediated self-cleavage were

TABLE 3

Figure 2:
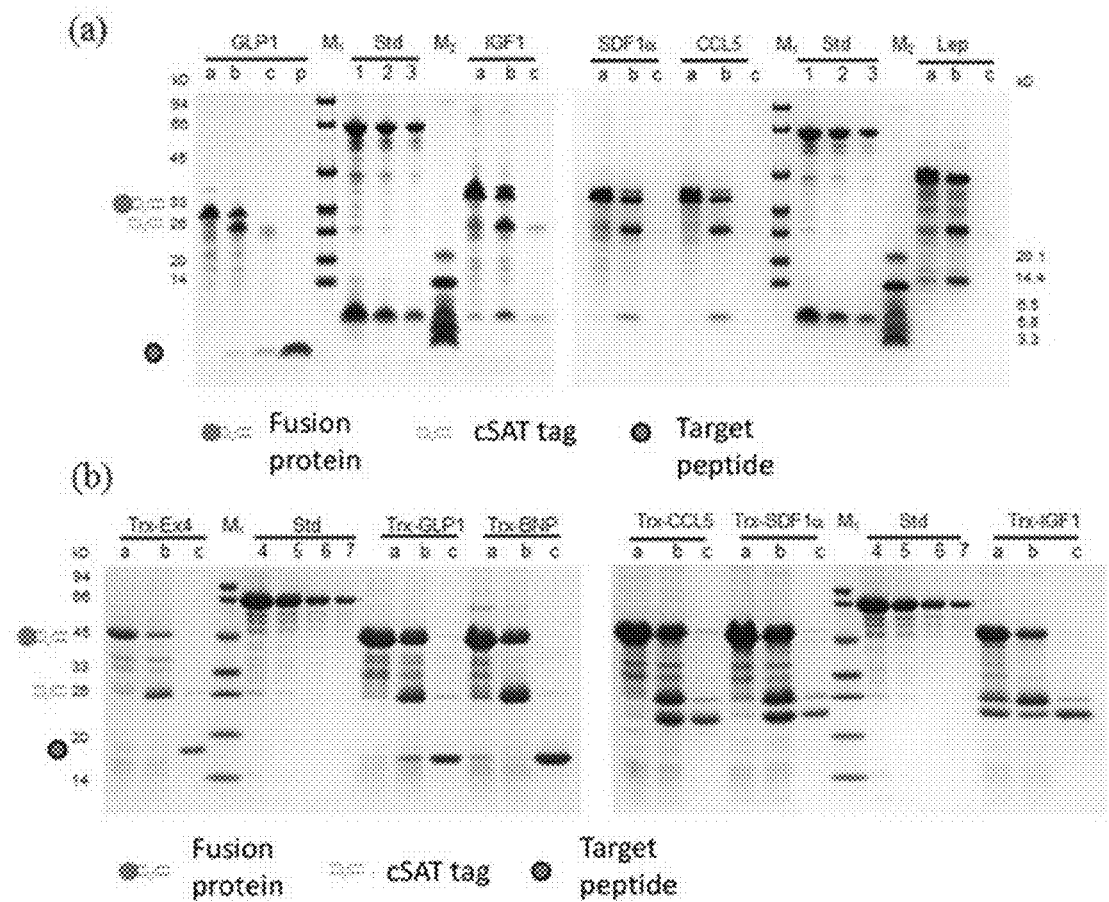

| Primer | Nucleotide sequence | SEQ ID NO | description |
|---|---|---|---|
| GLP1-F | 5'-AGCAT<u>CATATG</u>CATGCAGAAGGCACCTTT-3' | 33 | NdeI |
| Trx-GLP1-F | 5'-AGTCA<u>AGATCT</u>GGGTACCGACGACGACGACA AG CATGCAGAAGGCACCTTT-3' | 34 | BglII |
| GLP1-R | 5'-AGCAT<u>ACTAGT</u>GCATCTCCCGTGATGCAGAT ATCACCACGACCTTTAACCAG-3' | 35 | SpeI | respectively analyzed with 4-12% Bis-Tris SDS-PAGE or 12% Tris-Glycine SDS-PAGE for their protein compositions. The results were shown in FIG. 2. FIG. 2A shows the results of the expression and purification of target polypeptides without Trx tag; FIG. 2B shows the results of the expression and purification of target polypeptides with the Trx tag. Lane a: pellets after lysis of the bacteria cells; Lane b: pellets obtained by centrifugation after the intein-mediated self-cleavage of the fusion proteins; Lane c: supernatants obtained by centrifugation after the intein-mediated self-cleavage of the fusion proteins; Lane p: the samples after refined purification by HPLC; Lanes 1-3: standards for protein quantification (Std), in which the larger band is BSA (67 KD), with the loaded amount of 3 µg, 1.5 µg, and 0.75 µg, respectively; and the smaller band is Aprotinin (6.5 kD), with the loaded amount of 1.5 µg, 0.75 µg, and 0.3 µg, respectively; Lane 4-7: standards for protein quantification only containing BSA, with the loaded amount of 6 µg, 3, 1.5 µg, and 0.75 µg, respectively. The positions of the fusion protein; the Intein-ELK16 after cleavage and the target polypeptide are indicated. The molecular weight of each band of the protein MW markers M1 (14-94 kD) and M2 (3.3-20.1 kD) are indicated.

On the basis of the protein quantification standards, optical density analysis was carried out for the target bands using the Quantity ONE gel quantification analysis software (Bio-Rad), and the results were used to evaluate the yields of the aggregates formed by the fusion proteins, the yields of the target polypeptides released into the supernatants after intein-mediated self-cleavage as well as the purity of the target polypeptides in the supernatants. The results are shown in Table 4.

recovery was 46.8% and the yield was 1.8 µg/mg cell wet weight. Thus, GLP-1 in the suspension was further purified using reverse-phase HPLC. As shown in FIG. 2, the purity of the final product was over 95%, and the final yield was about 0.8 µg/mg cell wet weight.

(3) Although IGF1α, SDF-1α, CCL-5 and Leptin, when present in the fusion proteins with Intein-ELK16 respectively, were predominantly distributed in the aggregates, they were present in the insoluble pellets after intein-mediated self-cleavage.

Fusion Polypeptides with Trx Tag:

(1) Fusion proteins formed by each of six target polypeptides (GLP-1, Ex-4, BNP, CCL5, SDF-1α and IGF-1α) with Trx and Intein-ELK16 formed a large quantity of aggregates after expression, with the yields from 11.4-57.8 µg/mg cell wet weight. After intein-mediated self-cleavage, these polypeptides were released into the supernatants. The yields were 3.4-13.4 µg/mg cell wet weight, and the purities were 63.0%-79.7%. The result for the target polypeptide Lep was not shown in FIG. 2 because Lep expressed as a fusion with Trx still retained in the insoluble pellets after intein-mediated self-cleavage. Other solubility-enhancing peptide tags may be considered for the expression and purification of Lep.

(2) With respect to the improvement on solubility, the proportions of GLP-1, Ex-4, BNP and IGF-1α released into supernatants after intein-mediated self-cleavage were relatively high, with a recovery from 46.2-73.1%. The proportions of CCL5 and SDF-1α released into supernatants after intein-mediated self-cleavage were relatively low, with a recovery of 26.5% and 19.3%, respectively. It would also be possible to use other solubility-enhancing peptide tags to

TABLE 4

| Target polypeptide | Molecular weight (kD) | Amount of expressed arrogates[a] (µg/mg cell wet weight) | Yield of polypeptide[b] (µg/mg cell wet weight) | Efficiency of cleavage[c] (%) | Recovery[d] (%) | Purity of target polypeptide (%) |
|---|---|---|---|---|---|---|
| GLP-1 | 3.5 | 31.1 | 1.8 | 60.9 | 46.8 | 47.6 |
| CCL5[e] | 7.8 | 35.5 | 5.2 | 70.9 | 61.3 | 20.0 |
| SDF-1α[e] | 8.0 | 28.4 | 3.5 | 53.3 | 50.7 | 14.0 |
| IGF-1α[e] | 7.8 | 35.4 | 5.2 | 70.6 | 62.0 | 17.5 |
| Lep[e] | 16.2 | 44.6 | 10.5 | 60.3 | 60.3 | 23.0 |
| Trx-GLP-1 | 16.9 | 52.4 | 9.7 | 57.4 | 46.2 | 63.0 |
| Trx-BNP | 17.0 | 49.9 | 13.4 | 67.1 | 66.6 | 79.7 |
| Trx-Ex-4 | 17.7 | 11.4 | 3.4 | 75.3 | 73.1 | 78.8 |
| Trx-CCL5 | 21.2 | 57.8 | 7.0 | 44.8 | 26.5 | 73.0 |
| Trx-SDF-1α | 21.2 | 56.5 | 5.0 | 35.3 | 19.3 | 65.0 |
| Trx-IGF-1α | 21.2 | 34.0 | 9.2 | 67.8 | 59.4 | 77.2 |

[a] yields of protein aggregates and
[b] yields of target polypeptides after intein-mediated self-cleavage (calculated on the basis that 2.66 mg wet weight of *E. coli* cells was produced in 1 liter LB under an $OD_{600}$ of 2);
[c] efficiency of intein-mediated self-cleavage = 100% × (amount of aggregates before cleavage − amount of aggregates after cleavage)/amount of aggregates before cleavage;
[d] recovery = 100% × actual yield of target polypeptide/the theoretical yield of target peptide obtained when the aggregates are completely cleaved;
[e] the target polypeptides were present in the insoluble portion after intein-mediated self-cleavage.

Results

Fusion Polypeptides without Trx Tag:

(1) Five (GLP-1, CCL5, SDF-1α, IGF-1α and Lep) out of the seven polypeptides expressed as fusions with Intein-ELK16 can form a large quantity of aggregates, with the yields from 28.4-44.6 µg/mg cell wet weight. The results for the target polypeptides BNP and Ex-4 were not is shown in FIG. 2 because no protein expression can be found in the supernatants or pellets after cell lysis.

(2) The target polypeptide GLP-1 can be directly released into the suspension after intein-mediated self-cleavage. The increase the proportions of these two polypeptides that are released into the suspension after intein-mediated self-cleavage.

Example 4

Further Isolation and Purification of Polypeptides Through Cleavage by Enterokinase The target polypeptides (GLP-1, Ex-4, BNP, CCL5, SDF-1α and IGF-1α) fused with Trx, which were obtained from Example 3, were further isolated and purified.

First, the above mentioned Trx-peptide fusions that were released into the supernatants after intein-mediated self-cleavage were cleaved with Enterokinase (New England BioLabs, P8070S) according to the following steps:

The Intein cleavage buffer in the supernatants after intein-mediated self-cleavage was exchanged into Enterokinase cleavage buffer (20 mM Tris-HCl, 50 mM NaCl, 2 mM $CaCl_2$, pH 8.0) through ultrafiltration using ultrafilters (MW cut off: 3 Kd). Enterokinase (0.001% w/w) was added into the solution containing target fusions (e.g., 10 ng Enterokinase was added into 1 ml solution containing 1 mg/mL target fusions). The mixtures were incubated at 23° C. for 16 h, and then the samples cleaved by Enterokinase were stored under −70° C. for subsequent purification.

Figure 3:
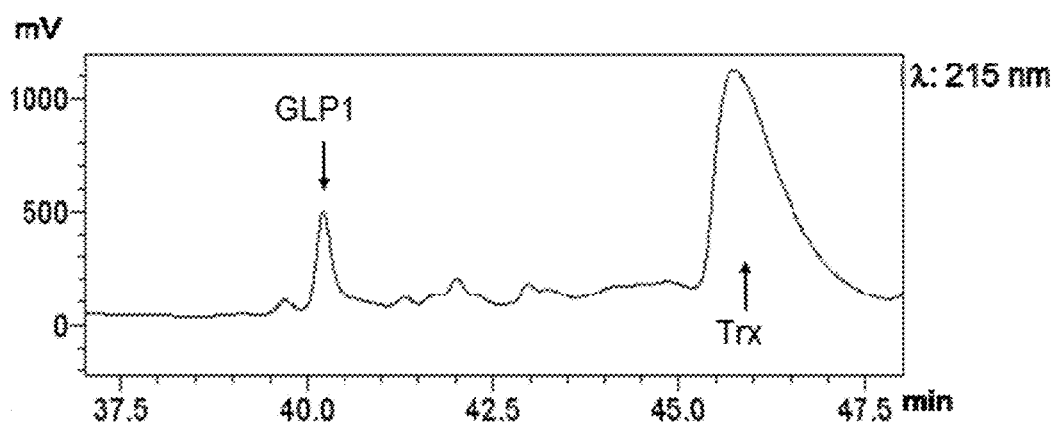
FIG. 3 shows the HPLC profile showing the separation of target protein CLP-1 from Trx.

Next, the Trx tag and the target polypeptide generated in the Enterokinase cleavage were further separated through reverse-phase HPLC. The detailed steps are as follows:

Mobile phase A (100% $H_2O$, containing 0.1% TFA) and mobile phase B (80% acetonitrile, containing 0.12% TFA) were set up. The HPLC chromatographic column (reverse phase C18 column; Diamonsil®, 99603) was equilibrated with the mobile phase containing 5% B at a flow rate of 1 mL/min. Gradient elution was used and the composition of mobile phase was increased from 5% B to 80% B during 60 min, meanwhile the absorbance was detected at wave length of 215 nm (the absorbance wave length characteristic for peptide bonds) and 280 nm (the absorbance wave length for conjugated double bonds in Tyr, Trp and Phe). During the elution, the fractions corresponding to absorption peaks were collected with the automatic collector of the HPLC system. The isolated fractions were lyophilized and stored at −20° C. The lyophilized samples were resuspended with water and analyzed with SDS-PAGE, and then further subjected to mass spectrometric detection. As an example, FIG. 3 shows the absorption peak profile during the separation of the sample produced by Enterokinase cleavage of Trx-GLP1, by reverse-phase HPLC.

Figure 4:
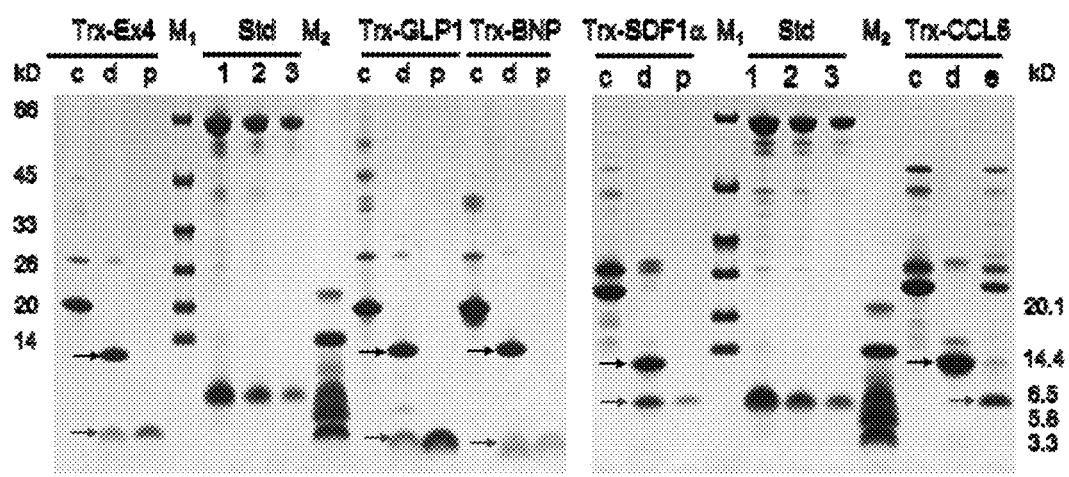
FIG. 4 shows the SDS-PAGE analysis of Enterokinase cleavage of the fusion protein Trx-target polypeptide-Intein-ELK16.
Figure 5:
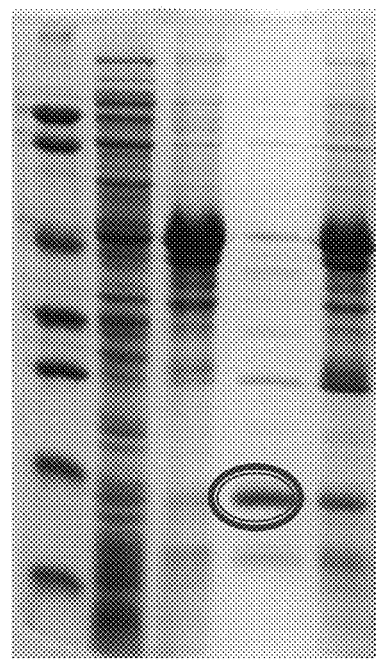
FIG. 5 shows the results of target polypeptide expression and purification with the combination of SUMO and ELK16.
Figure 6:
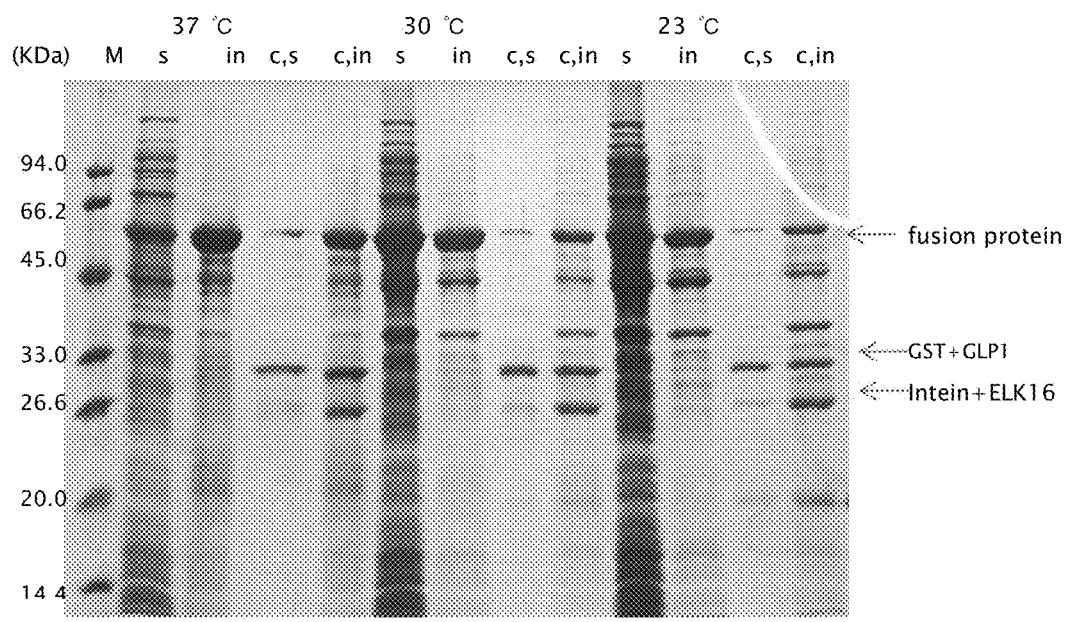
FIG. 6 shows the results of target polypeptide expression and purification with the combination of GST and ELK16.
Figure 7:
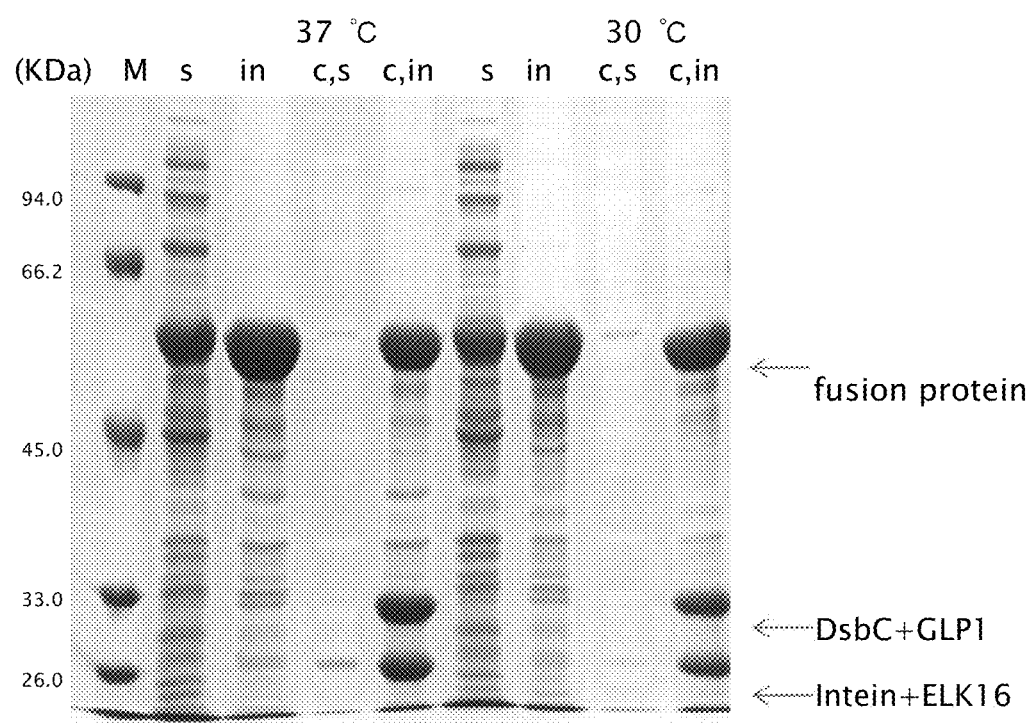
FIG. 7 shows the results of target polypeptide expression and purification with the combination of DsbC and ELK16.
Figure 8:
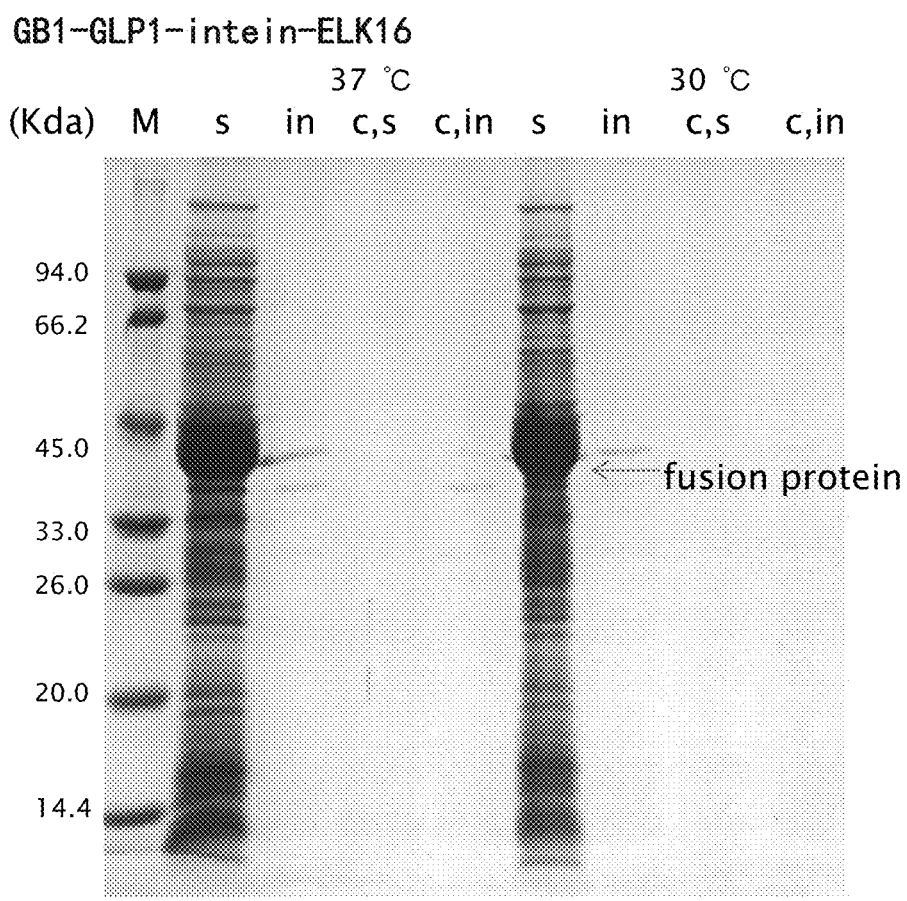
FIG. 8 shows the results of target polypeptide expression and purification with the combination of GB1 and ELK16.
Figure 9:
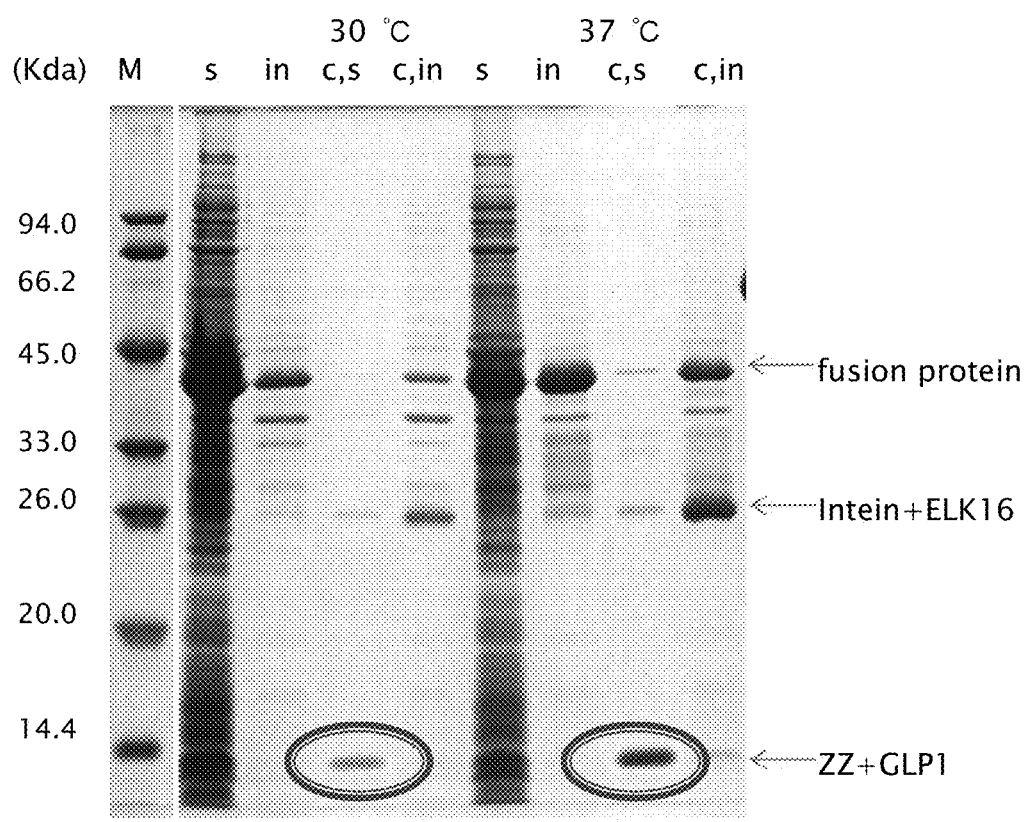
FIG. 9 shows the results of target polypeptide expression and purification with the combination of Z and ELK16.

The products before and after Enterokinase cleavage and after purification with reverse-phase HPLC were analyzed with 4-12% Bis-Tris SDS-PAGE for their protein composition. The results are shown in FIG. 4. Lane c: samples before Enterokinase cleavage; Lane d: samples after Enterokinase cleavage; Lane e: pellets after Enterokinase cleavage of Trx-CCL5; Lane p: samples after fine purification with reverse-phase HPLC; Lanes 1-3: standards for protein quantification (Std), in which the larger band is BSA (67 KD), with the loaded amount of 3 µg, 1.5 µg, and 0.75 µg, respectively, and the smaller band is Aprotinin (6.5 kD), with the loaded amount of 1.5 µg, 0.75 µg, and 0.3 µg, respectively. The black arrow indicates the Trx tag generated after Enterokinase cleavage, while the blue arrow indicates the target polypeptide generated after Enterokinase cleavage. The molecular weights of each band of the protein MW markers M1 (14-94 kD) and M2 (3.3-20.1 kD) are indicated.

On the basis of the protein quantification standards, optical density analysis was carried out for the target bands using the Bio-Rad Quantity ONE, and the results were used to evaluate the yields and purity of the target polypeptides in the samples.

Results (1) Under the above cleavage conditions, the efficiency of Enterokinase cleavage of Trx-GLP1, Trx-BNP, Trx-Ex4, Trx-SDF-1α and Trx-CCL5 reached almost 100%; correct bands for both Trx and target polypeptides were confirmed. Therefore, for the above target polypeptides, Enterokinase can be used for efficient and specific cleavage.

(2) For Trx-IGF-1α (data not shown), it was found that the bands after cleavage were not in the correct positions. It is believed that nonspecific cleavage occurred within the sequence of IGF-1α. Thus, IGF-1α might not be suitable for purification with Enterokinase cleavage.

(3) After removing Trx tag with Enterokinase cleavage, large amount of insoluble precipitates were present in the CCL5 sample. After centrifugation, the supernatants and precipitates were subjected to SDS-PAGE, respectively. It was found that CCL5 was only present in the insoluble fraction while the Trx tag was only present in the soluble fraction. This indicates that the solubility of CCL5 was enhanced when fused with Trx, but CCL5 in the fusion might not fold correctly, and thus it formed precipitates after the removal of the solubility-enhancing peptide tag Trx. Other solubility-enhancing peptide tags may be considered for the expression and purification of CCL5.

(4) After removing Trx tag by Enterokinase cleavage, GLP-1, BNP, Ex4 and SDF-1α can be recovered and purified with reverse-phase HPLC. The purities of the final products were over 95%, and the final yields were about 0.3-1.8 µg/mg cell wet weight. The detailed results are shown in Table 5.

TABLE 5

| Target polypeptide | Final yields according to different strategies (µg/mg cell wet weight) [a] | |
| --- | --- | --- |
| | Without Trx tag | With Trx tag |
| GLP-1 | 0.8 (2.6%) [b] | 1.1 (2.1%) [b] |
| BNP | No expression | 1.8 (3.6%) [b] |
| Ex-4 | No expression | 0.3 (1.7%) [b] |
| IGF-1α | insoluble | Nonspecific cleavage by EK |
| CCL5 | insoluble | Insoluble after EK cleavage |
| SDF-1α | insoluble | 0.2 (0.3%) [b] |
| Leptin | insoluble | insoluble |

[a] yields of target polypeptides after fine purification with HPLC (calculated on the basis that 2.66 ± 0.99 mg wet weight of *E. coli* cells was produced in per liter LB; quantification was performed with Pierce ® bicinchoninic acid (BCA) kit).
[b] The final recovery was listed in the brackets, as the ratio of the final yield of the target polypeptide to the amount of aggregates in Table 3.

The results from the above Examples demonstrate that a solubility-enhancing peptide tag can be used in combination with a self-aggregating peptide for the production and purification of polypeptides. Even if a solubility-enhancing peptide tag is added to the target polypeptide, the self-aggregating peptide can still mediate the fusion protein to form insoluble aggregates which are suitable for rapid purification through centrifugation or filtration. The addition of solubility-enhancing peptide tag may improve the expression of the polypeptide and increase the solubility of the target polypeptides.

Example 5

Production and Purification of Polypeptides Using Different Combinations of Solubility-Enhancing Peptide Tags and Self-Aggregating Peptides Solubility-Enhancing Peptide Tags Besides Trx, other 5 commonly used solubility-enhancing peptide tags (Table 6) were also selected for the production and purification of polypeptides in combination with self-aggregating peptide.

TABLE 6

| Solubility-enhancing peptide tags | Name | Size (kDa) | Amino acid sequence (SEQ ID NO) | Nucleotide sequence (SEQ ID NO) |
|---|---|---|---|---|
| Trx | thioredoxin | 11.8 | 36 | 37 |
| GST | glutathione-S-transferase | 25.5 | 38 | 39 |
| SUMO | small ubiquitin-related modifier | 10.9 | 40 | 41 |
| DsbC | disulfide bond isomerase | 23.5 | 42 | 43 |
| Z | single repeat of the IgG ZZ repeat domain of A protein | 14.5 | 44 | 45 |
| GB1 | G protein B1 domain | 6.5 | 46 | 47 |

Expression vectors of fusion proteins SUMO-Thymosin/BNP-Intein-ELK16, GST-GLP1-Intein-ELK16, DsbC-GLP1-Intein-ELK16, GB1-GLP1-Intein-ELK16 and Z-GLP1-Intein-ELK16 were constructed according to the methods as described in the above Examples. Recombinant expression and self-aggregating peptide based purification were performed as described above. The results of SDS-PAGE were shown in FIGS. 5-9. Lane s: the soluble fraction of the cell lysis; Lane in: the insoluble fraction of the cell lysis; Lane c,s: the soluble fraction of the fusion protein after cleavage; Lane c,in: the insoluble fraction of the fusion protein after cleavage. The results of expression and purification were summarized in Table 7.

TABLE 7

| Solubility-enhancing peptide tags | Target polypeptide | Expression of the intact fusion protein | Tag-target after self-cleavage |
|---|---|---|---|
| GST | GLP-1 | Insoluble (partial) | soluble |
| SUMO | Thymosin/BNP | Insoluble (partial) | soluble |
| DsbC | GLP-1 | Insoluble (largely partial) | insoluble |
| Z | GLP-1 | Insoluble (partial) | soluble |
| GB1 | GLP-1 | Soluble | — |

The results demonstrate that various solubility-enhancing peptide tags can be used for the production and purification of polypeptides in combination with self-aggregating peptides.

Self-Aggregating Peptides 18A and L6KD

Other two self-aggregating peptides 18A and L6KD, which have similar functions to ELK16, were also tested. Expression vectors of fusion proteins Trx-GLP1-Intein-18A and Trx-GLP1-Intein-L6KD were constructed according to the methods as described in the above Examples. Recombinant expression and self-aggregating peptide based purification were performed as described above. The results of SDS-PAGE were shown in FIG. 10. Lane s: the soluble fraction of the cell lysis; Lane in: the insoluble fraction of the cell lysis; Lane c,s: the soluble fraction of the fusion protein after cleavage; Lane c,in: the insoluble fraction of the fusion protein after cleavage. The results demonstrate that the self-aggregating peptides, 18A and L6KD, are also suitable for the methods of the invention.

REFERENCES

Leader B, et al. Protein therapeutics: a summary and pharmacological classification. Nat Rev Drug Discov, 2008, 7(1): 21-39.

Bray B L. Large-scale manufacture of peptide therapeutics by chemical synthesis. Nat Rev Drug Discov, 2003, 2(7):587-593.

Kamionka M. Engineering of therapeutic proteins production in Escherichia coli. Curr Pharm Biotechnol, 2011, 12(2): 268-274.

Demain A L, Vaishnav P. Production of recombinant proteins by microbes and higher organisms. Biotechnol Adv, 2009, 27(3):297-306.

Walsh G. Biopharmaceutical benchmarks 2006. Nat Biotechnol, 2006, 24(7):769-776.

Walsh G. Biopharmaceutical benchmarks 2003. Nat Biotechnol, 2003, 21(8):865-870.

Kuliopulos A, Walsh C T. Production, purification, and cleavage of tandem repeats of recombinant peptides. J Am Chem Soc, 1994, 116(11):4599-4607.

Hannig G, Makrides S C. Strategies for optimizing heterologous protein expression in Escherichia coli. Trends Biotechnol, 1998, 16(2):54-60.

Murby M, et al. Upstream strategies to minimize proteolytic degradation upon recombinant production in Escherichia coli. Protein Expr Purif, 1996, 7(2):129-136.

Hao Chen et al. China Biotechnology, 2002, 22(5): p. 87-92.

Zhao X B, et al. Molecular self-assembly and applications of designer peptide amphiphiles. Chem Soc Rev, 2010, 39: 3480-3498.

Mitraki A. Protein aggregation: from inclusion bodies to amyloid and biomaterials, in Advances in Protein Chemistry and Structural Biology. Elsevier Academic Press Inc: San Diego, 2010, 79: 89-125.

Wu X Y, et al. E W, a novel recombinant analogue of exendin-4 expressed in Escherichia coli. Scientific Research and Essays Vol. 6(14), pp. 2941-2949, 18 Jul., 2011.

Sun Z Y, et al. Use of Ssp dnaB derived mini-intein as a fusion partner for production of recombinant human brain natriuretic peptide in Escherichia coli. Protein Expression and Purification 43 (2005) 26-32.

Bosse-Doenecke, et al. High yield production of recombinant native and modified peptides exemplified by ligands for G-protein coupled receptors. Protein Expression and Purification 58 (2008) 114-121.

Proudfoot, et al. Extension of Recombinant Human RANTES by the Retention of the Initiating Methionine Produces a Potent Antagonist. THE JOURNAL OF BIOLOGICAL CHEMISTRY Vol. 271, No. 5, Issue of February 2, pp. 2599-2603, 1996

Cho, et al. Maltose binding protein facilitates high-level expression and functional purification of the chemokines RANTES and SDF-1α from Escherichia coli. Protein Expression and Purification 60 (2008) 37-45

Zhang, et al. High-level soluble expression of hIGF-1 fusion protein in recombinant Escherichia coli. Process Biochemistry 45 (2010) 1401-1405

Gertler, et al. Large-scale preparation of biologically active recombinant ovine obese protein (leptin). FEBS Letters 422 (1998) 137-140.

Leder et al. New methods for efficient protein production in drug discovery. Current Opinion in Drug Discovery & Development 2007 10(2):193-202.

Esposito and Chatterjee Enhancement of soluble protein expression through the use of fusion tags. Current Opinion in Biotechnology 2006, 17:353-358.

Waugh, Making the most of affinity tags. TRENDS in Biotechnology Vol. 23 No. 6 Jun. 2005.

Wu et al. Protein trans-splicing and functional mini-inteins of a cyanobacterial dnaB intein. Biochimica et Biophysica Acta 1387 (1998) 422-432.

TELENTI et al. The Mycobacterium xenopi GyrA Protein Splicing Element: Characterization of a Minimal Intein. JOURNAL OF BACTERIOLOGY, October 1997, p. 6378-6382.

Zhang et al. Spontaneous assembly of a self-complementary oligopeptide to form a stable microscopic membrane. Proc. Natl. Acad. Sci. USA (1993) Vol 90, pp. 3334-3338.

The invention claimed is:

1. A polynucleotide which comprises a nucleotide sequence encoding a fusion protein, or the complement thereof, wherein said fusion protein comprises a solubility-enhancing peptide tag moiety, a self-aggregating peptide moiety and a target polypeptide moiety, wherein said target polypeptide moiety is located between said solubility-enhancing peptide tag moiety and said self-aggregating peptide moiety, and said target polypeptide moiety is attached to said self-aggregating peptide moiety through a first linker comprising a first cleavage site, wherein said fusion proteins, upon expression in a host cell, are capable of forming active aggregates through said self-aggregating peptide moiety, wherein said self-aggregating peptide comprises an amphipathic self-assembling short peptide selected from the group consisting of amphipathic β-sheet short peptides, amphipathic α-helix short peptides and surfactant-like short peptides.

2. An expression construct which comprises the polynucleotide according to claim 1.

3. A host cell which comprises the polynucleotide according to claim 1, wherein said host cell is capable of expressing said fusion protein.

4. A method for production and purification of a target polypeptide, said method comprises the steps of:
  (a) culturing the host cell according to claim 3 so as to express said fusion protein;

(b) lysing said host cells, then removing the soluble portion of the cell lysis and collecting the insoluble portion;

(c) releasing the soluble target polypeptide with the solubility-enhancing peptide tag from said insoluble portion by cleaving the first cleavage site; and (d) removing the insoluble portion formed in step (c) and recovering the soluble portion containing said target polypeptide.

5. The method according claim 4, further comprising:

(e) if a second cleavage site is present, cleaving said second cleavage site so as to separate said target polypeptide from said solubility-enhancing peptide tag;

(f) removing said solubility-enhancing peptide tag and collecting the purified target polypeptide.

6. A host cell which has been transformed with the expression construct according to claim 2, wherein said host cell is capable of expressing said fusion protein.

7. The polynucleotide according to claim 1, wherein said self-aggregating peptide moiety comprises one said amphipathic β-sheet short peptide.

8. The polynucleotide according to claim 1, wherein said self-aggregating peptide moiety comprises a tandem repeat of two or more of said amphipathic β-sheet short peptides.

9. The polynucleotide according to claim 7, wherein said amphipathic β-sheet short peptide is 4-30 amino acid residues in length.

10. The polynucleotide according to claim 7, wherein 40%-80% of the amino acid residues in said amphipathic β-sheet short peptide are hydrophobic amino acids.

11. The polynucleotide according to claim 10, wherein said amphipathic β-sheet short peptide comprises an amino acid sequence as set forth in SEQ ID NO:1.

12. The polynucleotide according to claim 1, wherein the self-aggregating peptide moiety comprises one repeat of amphipathic α-helix short peptide.

13. The polynucleotide according to claim 1, wherein the self-aggregating peptide moiety comprises a tandem repeat of two or more said amphipathic α-helix short peptide.

14. The polynucleotide according to claim 12, wherein said amphipathic α-helix short peptide is 4-30 amino acid residues in length.

15. The polynucleotide according to claim 12, wherein 40%-80% of the amino acid residues in said amphipathic α-helix short peptide are hydrophobic amino acids.

16. The polynucleotide according to claim 15, wherein said amphipathic α-helix short peptide comprises an amino acid sequence as set forth in SEQ ID NO:2.

17. The polynucleotide according to claim 1, wherein said surfactant-like short peptide is 7-30 amino acids in length and comprises an amino acid sequence represented by the following general formula from N-terminal to C-terminal:

A-B or B-A wherein A is a peptide consisting of hydrophilic amino acid residues, said hydrophilic amino acid residues may be the same or different, and are selected from the group consisting of Lys, Asp, Arg, Glu, His, Ser, Thr, Asn and Gln;

B is a peptide consisting of hydrophobic amino acids, said hydrophobic amino acid residues may be the same or different, and are selected from the group consisting of Leu, Gly, Ala, Val, Ile, Phe and Trp;

A and B are linked by a peptide bond; and the proportion of hydrophobic amino acid residues in said surfactant-like short peptide is 55%-95%.

18. The polynucleotide according to claim 17, wherein said surfactant-like short peptide is 8 amino acid residues in length, wherein the proportion of hydrophobic amino acid residues is 75%.

19. The polynucleotide according to claim 18, wherein said surfactant-like short peptide consists of an amino acid sequence as set forth in SEQ ID NO:3, SEQ ID NO:4 or SEQ ID NO:5.

20. The polynucleotide according to claim 1, wherein said self-aggregating peptide moiety is located at the C-terminal of said fusion protein.

21. The polynucleotide according to claim 1, wherein said solubility-enhancing peptide tag is selected from the group consisting of N-utilization substance A (NusA), Glutathione-S-transferase (GST), Thioredoxin (Trx), Small ubiquitin like modifier (SUMO), Disulfide bond C (DsbC), Protein A IgG ZZ repeat domain (Z), Protein G B1 domain (GB1), Maltose binding protein (MBP) and Phage T7 protein kinase (T7PK).

22. The polynucleotide according to claim 1, wherein said first cleavage site is selected from the group consisting of a chemical cleavage site, an enzymatic cleavage site and a self-cleavage site.

23. The polynucleotide according to claim 22, wherein said self-cleavage site comprises an intein.

24. The polynucleotide according to claim 23, wherein said intein is Mxe GyrA having the sequence as set forth in SEQ ID NO:6.

25. The polynucleotide according to claim 24, wherein said Mxe GyrA is directly attached to the C-terminal of said target polypeptide.

26. The polynucleotide according to claim 1, wherein said first linker further comprises a spacer.

27. The polynucleotide according to claim 1, wherein said target polypeptide is attached to said solubility-enhancing peptide tag through a second linker.

28. The polynucleotide according to claim 27, wherein said second linker comprises a spacer.

29. The polynucleotide according to claim 27, wherein said second linker comprises a second cleavage site, wherein the cleavage condition for said second cleavage site is different from the cleavage condition for said first cleavage site.

30. The polynucleotide according to claim 29, wherein said second cleavage site is selected from the group consisting of a second chemical cleavage site, a second enzymatic cleavage site and a second self-cleavage site.

31. The polynucleotide according to claim 30, wherein said second enzymatic cleavage site comprises an Enterokinase recognition sequence as set forth in SEQ ID NO:7.

32. The polynucleotide according to claim 31, wherein said Enterokinase recognition sequence is directly attached to the N-terminal of said target polypeptide.

33. The polynucleotide according to claim 29, wherein said second linker further comprises a spacer.

34. The polynucleotide according to claim 1, wherein said target polypeptide is 30-100 amino acid residues in length.

\* \* \* \* \*